United States Patent
Lindenschmidt et al.

(10) Patent No.: US 7,652,143 B2
(45) Date of Patent: Jan. 26, 2010

(54) CYCLIC UREAS USED AS INHIBITORS OF METALLOPROTEASES

(75) Inventors: Andreas Lindenschmidt, Bad Soden (DE); Holger Wagner, Biberach/Mettenberg (DE); Jochen Beninga, Mainz (DE); Sven Grueneberg, Kelkheim (DE); Klaus-ulrich Weithmann, Hofheim (DE)

(73) Assignee: sanofi-aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 11/763,618

(22) Filed: Jun. 15, 2007

(65) Prior Publication Data

US 2008/0096918 A1  Apr. 24, 2008

Related U.S. Application Data

(63) Continuation of application No. PCT/EP2005/012799, filed on Dec. 1, 2005.

(30) Foreign Application Priority Data

Dec. 15, 2004 (DE) .................. 10 2004 060 229

(51) Int. Cl.
 C07D 401/00 (2006.01)
 C07D 233/00 (2006.01)
 A61K 31/17 (2006.01)

(52) U.S. Cl. ............. 546/272.7; 514/311; 514/341; 514/362; 514/386; 514/389; 514/824; 514/825; 514/237.5; 546/152; 548/318.5; 548/317.1; 548/323.5; 548/134

(58) Field of Classification Search ........... 514/237.5, 514/311, 341, 362, 386, 389, 824, 825, 826; 546/152, 272.7; 548/317.1, 318.5, 323.5
 See application file for complete search history.

(56) References Cited

U.S. PATENT DOCUMENTS

| 6,218,389 B1 | 4/2001 | Almstead et al. |
| 6,376,506 B1 | 4/2002 | Broka et al. |
| 6,495,548 B1 | 12/2002 | Duan |
| 6,927,216 B2 | 8/2005 | Cherney et al. |

FOREIGN PATENT DOCUMENTS

| IN | 2003MU00236 | * | 2/2003 |
| WO | WO 98/32748 | | 7/1998 |
| WO | WO 2005077937 | | 8/2005 |

* cited by examiner

*Primary Examiner*—Ardin Marschel
*Assistant Examiner*—Savitha Rao
(74) *Attorney, Agent, or Firm*—James W. Bolcsak

(57) ABSTRACT

The present invention relates to a novel compound of the formula I:

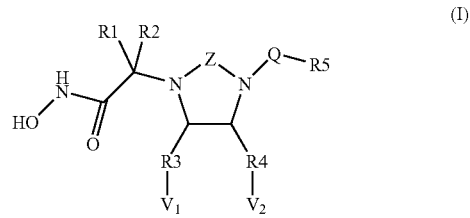

and/or all stereoisomeric forms of the compound of the formula I and/or mixtures of these forms in any ratio, and/or a physiologically tolerated salt of the compound of the formula I, in which R1 to R5 and V1, V2 have the meanings stated in the claims and specification. The inventive compounds are suitable as inhibitors of metalloproteases, especially of ADAMTS proteases and TNF-α converting enzyme (TACE), and for the treatment of disorders such as but not limited to osteoarthrosis and rheumatoid arthritis.

2 Claims, No Drawings

CYCLIC UREAS USED AS INHIBITORS OF METALLOPROTEASES

FIELD OF THE INVENTION

The present invention relates to cyclic ureas which are suitable for use as inhibitors of metalloproteases, especially of ADAMTS proteases and TNF-α converting enzyme (TACE), to methods for the preparation thereof and to the use thereof for the treatment of disorders such as osteoarthrosis and rheumatoid arthritis.

BACKGROUND OF THE INVENTION

In the pathological state of osteoarthrosis, degradation of the aggrecan, the main proteoglycan of articular cartilage, represents a very early and crucial event. The pathological loss of the cartilage aggrecan results from proteolytic cleavages in its interglobular domain. Amino acid sequence analyses of proteoglycan metabolites isolated from the synovial fluid of patients suffering from joint damage, osteoarthrosis or an inflammatory joint disorder have shown that a proteolytic cleavage takes place preferentially between the amino acids Glu$^{373}$ and Ala$^{374}$ in the interglobular domain of human aggrecan (Lohmander et al., Arthritis Rheum. 36, (1993), 1214-1222). The proteolytic activity responsible for this cleavage is referred to as "aggrecanase" and may be assigned to the superfamily of metalloproteinases (MP).

Zinc is essential in the catalytically active site of metalloproteinases. MPs cleave collagen, laminin, proteoglycans, elastin or gelatin under physiological conditions and therefore play an important role in bone and connective tissue. A large number of different MP inhibitors are known (J. S. Skotnicki et al., Ann. N.Y. Acad. Sci. 878, 61-72 (1999); EP 0 606 046; WO94/28889). Some of these inhibitors are not well characterized in relation to their specificity; others are more or less selectively directed in particular against matrix metalloproteinases (MMPs).

Aggrecanase differs from matrix metalloproteinases (MMPs) by its different specificity, which is directed against particular cleavage sites which occur in aggrecan and are not favored by MMPs. The cleavage results in characteristic fragments which can be detected by using suitable antibodies.

A frequent disadvantage of known inhibitors of MMPs is the lack of specificity of the inhibition for only one class of MMPs. Most MMP inhibitors therefore inhibit a plurality of MMPs simultaneously.

In the endeavor to find effective compounds for the treatment of connective issue disorders, it has now been found that the compounds of the formula I are strong inhibitors of matrix metalloproteinases such as aggrecanase, for example ADAMTS-4, ADATMS-5 or ADAMTS-1 and tissue necoris factor α (TNF-α) converting enzyme.

DETAILED DESCRIPTION OF THE INVENTION

The invention therefore relates to a compound of the formula I

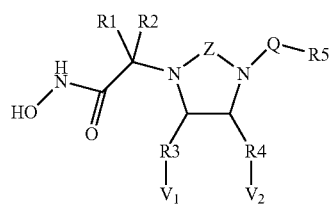

(I)

and/or all stereoisomeric forms of the compound of the formula I and/or mixtures of these forms in any ratio, and/or a physiologically tolerated salt of the compound of the formula I, where Z is —C(O)— or —S(O)$_2$—, R1 and R2 are identical or different and are independently of one another
  a) hydrogen atom,
  b) —(C$_1$-C$_6$)-alkyl,
  c) —(C$_3$-C$_6$)-cycloalkyl,
  d) —(C$_2$-C$_4$)-alkyl-Het, in which Het is a mono- or bicyclic 4- to 15-membered heterocycle which comprises at least one carbon atom and one, two, three or four heteroatoms from the series nitrogen, sulfur or oxygen, in which the heterocycle is unsubstituted or substituted once, twice or three times by R8, or
  e) —(C$_2$-C$_4$)-alkyl-(C$_6$-C$_{14}$)-aryl in which aryl is unsubstituted or substituted once or twice by R8, or R1 and R2 form together with the carbon atom to which they are respectively bonded
  a) —(C$_3$-C$_6$)-cycloalkyl or
  b) a mono- or bicyclic 4- to 15-membered heterocycle which comprises at least one carbon atom and one, two, three or four heteroatoms from the series nitrogen, sulfur or oxygen, in which the heterocycle is unsubstituted or substituted once, twice or three times by R8, R3 and R4 are identical or different and are independently of one another
  a covalent bond, —(CH$_2$)$_m$—, —(C$_1$-C$_3$)-alkylene-O—(C$_0$-C$_3$)-alkylene, —(C$_0$-C$_3$)-alkylene-C(O)—O—(CH$_2$)$_n$—, —(C$_0$-C$_3$)-alkylene-C(O)—NR$^{10}$—(CH$_2$)$_n$—,
  —(CH$_2$)$_m$—CH(OH)—(CH$_2$)$_n$—, —(C$_1$-C$_3$)-alkylene-N(R$^{10}$)—(CH$_2$)$_n$—, —(CH$_2$)$_m$—NR$^{10}$—C(O)—(CH$_2$)$_n$—,
  —(CH$_2$)$_m$—NR$^{10}$—C(O)—NR$^{10}$—(CH$_2$)$_n$—, —(CH$_2$)$_m$—O—C(O)—NR$^{10}$—(CH$_2$)$_n$—,
  —(CH$_2$)$_m$—NR$^{10}$—C(O)—O—(CH$_2$)$_n$—, —(CH$_2$)$_m$—S—(CH$_2$)$_n$—, —(C$_1$-C$_3$)-alkylene-S(O)—(CH$_2$)$_n$—,
  —(C$_1$-C$_3$)-alkylene-SO$_2$—(CH$_2$)$_n$—, —(C$_1$-C$_3$)-alkylene-SO$_2$—NH—(R$^{10}$),
  —(CH$_2$)$_m$—SO$_2$—NR$^{10}$—(CH$_2$)$_n$—, —(CH$_2$)$_m$—NR$^{10}$—SO$_2$—(CH$_2$)$_n$— or —(CH$_2$)$_m$—NR$^{10}$—SO$_2$—NR$^{10}$—(CH$_2$)$_n$—, in which
  n and m are independently of one another identical or different, and m is the integers 1, 2, 3, 4, 5 or 6, and n is the integers zero 1, 2, 3, 4, 5 or 6, and in which the alkylene radicals which are formed by —(CH$_2$)$_m$— or —(CH$_2$)$_n$— are unsubstituted or substituted once, twice or three times by halogen, —NH$_2$ or —OH or form a —(C$_3$-C$_6$)-cycloalkyl in which cycloalkyl is unsubstituted or substituted once, twice or three times by halogen, —NH$_2$ or —OH, R$^{10}$ is hydrogen atom, —(C$_1$-C$_6$)-alkyl, —(C$_0$-C$_4$)-alkyl-OH, —(C$_0$-C$_4$)-alkyl-O—(C$_1$-C$_4$)-alkyl or —(C$_1$-C$_3$)-perfluoroalkyl, V$_1$, V$_2$ and R5 are identical or different and are independently of one another
  a) hydrogen atom,
  b) —(C$_6$-C$_{14}$)-aryl in which aryl is unsubstituted or substituted once or twice by R8 or the radical -G-M, or
  c) a mono- or bicyclic 4- to 15-membered heterocycle which comprises at least one carbon atom and one, two, three or four heteroatoms from the series nitrogen, sulfur or oxygen, in which the heterocycle is unsubstituted or substituted once, twice or three times by R8 or the radical -G-M, M is a) hydrogen atom,
  b) —($C_6$-$C_{14}$)-aryl in which aryl is unsubstituted or substituted once or twice by R8, or
  c) a mono- or bicyclic 4- to 15-membered heterocycle which comprises at least one carbon atom and one, two, three or four heteroatoms from the series nitrogen, sulfur or oxygen, and in which the heterocycle is unsubstituted or substituted once, twice or three times by R8, R8 is 1) halogen,
  2) —$NO_2$,
  3) —CN,
  4) —C(O)—$NH_2$,
  5) —$SO_2$—$NH_2$,
  6) —OH,
  7) —$NH_2$,
  8) —O—$CF_3$,
  9) —($C_6$-$C_{14}$)-aryl in which aryl is unsubstituted or substituted once or twice by halogen or —O—($C_1$-$C_8$)-alkyl,
  10) —($C_1$-$C_8$)-alkyl in which alkyl is unsubstituted or substituted once, twice or three times by halogen, $NH_2$, —OH or methoxy,
  11) —O—($C_1$-$C_8$)-alkyl in which alkyl is unsubstituted or substituted once, twice or three times by halogen, $NH_2$, —OH or methoxy,
  12) —$SO_2$—$CH_3$ or
  13) —$SO_2$—$CF_3$, G is covalent bond, —($CH_2$)$_o$—, —($C_0$-$C_3$)-alkylene-O—($C_0$-$C_3$)-alkylene-, —($C_0$-$C_3$)-alkylene-C(O)—O—($CH_2$)$_p$—, —($C_0$-$C_3$)-alkylene-C(O)—$NR^{10}$—($CH_2$)$_p$—, —($CH_2$)$_o$—CH(OH)—($CH_2$)$_p$—, —($C_0$-$C_3$)-alkylene-N($R^{10}$)—($CH_2$)$_p$—, —($CH_2$)$_o$—$NR^{10}$—C(O)—($CH_2$)$_p$—, —($CH_2$)$_o$—$NR^{10}$—C(O)—$NR^{10}$—($CH_2$)$_p$—, —($CH_2$)$_o$—O—C(O)—$NR^{10}$—($CH_2$)$_p$—, —($CH_2$)$_o$—$NR^{10}$—C(O)—O—($CH_2$)$_p$—, —($CH_2$)$_o$—S—($CH_2$)$_p$—, —($C_0$-$C_3$)-alkylene-S(O)—($CH_2$)$_p$—, —($C_0$-$C_3$)-alkylene-$SO_2$—($CH_2$)$_p$—, —($C_0$-$C_3$)-alkylene-$SO_2$—NH—($R^{10}$), —($CH_2$)$_o$—$SO_2$—$NR^{10}$—($CH_2$)$_p$—, —($CH_2$)$_o$—$NR^{10}$—$SO_2$—($CH_2$)$_p$—, —($C_0$-$C_3$)-alkylene-O—($C_2$-$C_4$)-alkenylene- or —($CH_2$)$_o$—$NR^{10}$—$SO_2$—$NR^{10}$—($CH_2$)$_p$—, in which
  o and p are identical or different and are independently of one another the integers zero, 1, 2, 3, 4, 5 or 6, and in which the alkylene radicals which are formed by —($CH_2$)$_o$— or —($CH_2$)$_p$— are unsubstituted or substituted once, twice or three times by halogen, —$NH_2$ or —OH or form a —($C_3$-$C_6$)-cycloalkyl in which cycloalkyl is unsubstituted or substituted once, twice or three times by halogen, —$NH_2$ or —OH, and R10 is as defined above, and Q is covalent bond, —($C_1$-$C_3$)-alkylene or —($C_3$-$C_6$)-cycloalkyl, on condition that at least one of the radicals $V_1$, $V_2$ or R5 is —($C_6$-$C_{14}$)-aryl or a mono- or bicyclic 4- to 15-membered heterocycle, in which aryl or heterocycle are unsubstituted or substituted once or twice by R8 or the radical -G-M.

2) The invention further relates to the compound of the formula I where
Z is —C(O)— or —S(O)$_2$—,
R1 and R2 are identical or different and are independently of one another hydrogen atom or
  —($C_1$-$C_4$)-alkyl, or
R1 and R2 form together with the carbon atom to which they are respectively bonded
  —($C_3$-$C_6$)-cycloalkyl, R3 and R4 are identical or different and are independently of one another
  a covalent bond, —($CH_2$)$_m$—, —($C_1$-$C_3$)-alkylene-O—($C_0$-$C_3$)-alkylene-, —($C_0$-$C_3$)-alkylene-C(O)—O—($CH_2$)$_n$—, —($C_0$-$C_2$)-alkylene-C(O)—$NR^{10}$—($CH_2$)$_n$—, —($CH_2$)$_m$—CH(OH)—($CH_2$)$_n$—, —($C_1$-$C_3$)-alkylene-N($R^{10}$)—($CH_2$)$_n$—, —($CH_2$)$_m$—$NR^{10}$—C(O)—($CH_2$)$_n$—, —($CH_2$)$_m$—$NR^{10}$—C(O)—$NR^{10}$—($CH_2$)$_n$—, —($CH_2$)$_m$—O—C(O)—$NR^0$—($CH_2$)$_n$—, —($CH_2$)$_m$—$NR^{10}$—C(O)—O—($CH_2$)$_n$—, —($CH_2$)$_m$—S—($CH_2$)$_n$—, —($C_1$-$C_3$)-alkylene-S(O)—($CH_2$)$_n$—, —($C_1$-$C_3$)-alkylene-$SO_2$—($CH_2$)$_n$—, —($C_1$-$C_3$)-alkylene-$SO_2$—NH—($R^{10}$), —($CH_2$)$_m$—$SO_2$—$NR^{10}$—($CH_2$)$_n$—, —($CH_2$)$_m$—$NR^{10}$—$SO_2$—($CH_2$)$_n$— or —($CH_2$)$_m$—$NR^{10}$—$SO_2$—$NR^{10}$—($CH_2$)$_n$—, in which
  n and m are independently of one another identical or different, and m is the integers 1, 2, 3, 4, 5 or 6, and n is the integers zero, 1, 2, 3, 4, 5 or 6, and in which the alkylene radicals which are formed by —($CH_2$)$_m$— or —($CH_2$)$_n$— are unsubstituted or substituted once, twice or three times by halogen, —$NH_2$ or —OH or form a —($C_3$-$C_6$)-cycloalkyl in which cycloalkyl is unsubstituted or substituted once, twice or three times by halogen, —$NH_2$ or —OH, $R^{10}$ is hydrogen atom, —($C_1$-$C_6$)-alkyl, —($C_0$-$C_4$)-alkyl-OH, —($C_0$-$C_4$)-alkyl-O—($C_1$-$C_4$)-alkyl or —($C_1$-$C_3$)-perfluoroalkyl, $V_1$, $V_2$ and R5 are identical or different and are independently of one another
  a) hydrogen atom,
  b) —($C_6$-$C_{14}$)-aryl in which aryl is a radical from the series phenyl, naphthyl, 1-naphthyl, 2-naphthyl, anthryl or fluorenyl, is unsubstituted or substituted once or twice by R8 or the radical -G-M, or
  c) a mono- or bicyclic 4- to 15-membered heterocycle in which heterocycle is a radical from the series acridinyl, azetidinyl, benzimidazolyl, benzodioxol, benzodiazin, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, beta-carbolinyl, quinazolinyl, quinolinyl, 4H-quinolizinyl, quinoxalinyl, quinuclidinyl, chromanyl, chromenyl, decahydroquinolinyl, dihydrofuran, dithiazinyl, dithiazolly, fuaranyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyro-azolidinyl, pyrazolinyl, pyrazolyl, pyridazinyl, pryidooxazolyl, pyridoimidazolyl, pyridothiazolyl, pyridothiophenyl, pyridyl, pyrimidinyl, pyrrolidinyl, pyrrolinyl, pyrrolyl, tetrahydrofuranyl, tetrahydroisoquinolinyl, tetrahydroquinolinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, triazinyl, 1,2,3-triazolyl, 1,2,4-triazolyl, 1,2,5-triazolyl, 1,3,4-triazolyl and xanthenyl, in which the heterocycle is unsubstituted or substituted once, twice or three times by R8 or the radical -G-M, M is a) hydrogen atom,
b) —($C_6$-$C_{14}$)-aryl in which aryl is as defined above and is unsubstituted or substituted once or twice by R8, or
c) a mono- or bicyclic 4- to 15-membered heterocycle in which heterocycle is as defined above, and in which the heterocycle is unsubstituted or substituted once, twice or three times by R8, $R^8$ is 1) halogen,
2) —$NO_2$,
3) —CN,
4) —C(O)—$NH_2$,
5) —$SO_2$—$NH_2$,
6) —OH,
7) —$NH_2$,
8) —O—$CF_3$,
9) —($C_6$-$C_{14}$)-aryl in which aryl is unsubstituted or substituted once or twice by halogen or —O—($C_1$-$C_8$)-alkyl,
10) —($C_1$-$C_8$)-alkyl in which alkyl is unsubstituted or substituted once, twice or three times by halogen, $NH_2$, —OH or methoxy,
11) —O—($C_1$-$C_8$)-alkyl in which alkyl is unsubstituted or substituted once, twice or three times by halogen, $NH_2$, —OH or methoxy,
12) —$SO_2$—$CH_3$ or
13) —$SO_2$—$CF_3$, G is covalent bond, —($CH_2$)$_o$—, —($C_0$-$C_3$)-alkylene-O—($C_0$-$C_3$)-alkylene, —($CH_2$)$_o$—CH(OH)—($CH_2$)$_p$—, —($C_0$-$C_3$)-alkylene-C(O)—O—($CH_2$)$_p$—, —($C_0$-$C_3$)-alkylene-C(O)—$NR^{10}$—($CH_2$)$_p$—, —($C_0$-$C_3$)-alkylene-N($R^{10}$)—($CH_2$)$_p$—, —($CH_2$)$_o$—$NR^{10}$—C(O)—($CH_2$)$_p$—, —($CH_2$)$_o$—O—C(O)—$NR^{10}$—($CH_2$)$_p$—, —($CH_2$)$_o$—$NR^{10}$—C(O)—$NR^{10}$—($CH_2$)$_p$—, —($CH_2$)$_o$—$NR^{10}$—C(O)—O—($CH_2$)$_p$—, —($CH_2$)$_o$—S—($CH_2$)$_p$—, —($C_0$-$C_3$)-alkylene-S(O)—($CH_2$)$_p$—, —($C_0$-$C_3$)-alkylene-$SO_2$—($CH_2$)$_p$—, —($C_0$-$C_3$)-alkylene-$SO_2$—NH—($R^{10}$), —($CH_2$)$_o$—$SO_2$—$NR^{10}$—($CH_2$)$_p$—, —($CH_2$)$_o$—$NR^{10}$—$SO_2$—($CH_2$)$_p$—, —($C_0$-$C_3$)-alkylene-O—($C_2$-$C_4$)-alkenylene-, or —($CH_2$)$_o$—$NR^{10}$—$SO_2$—$NR^{10}$—($CH_2$)$_p$—, in which
o and p are identical or different and are independently of one another the integers zero, 1, 2, 3, 4, 5 or 6, and in which the alkylene radicals which are formed by —($CH_2$)$_o$— or —($CH_2$)$_p$— are unsubstituted or substituted once, twice or three times by halogen, —$NH_2$ or —OH or —($C_3$-$C_6$)-cycloalkyl in which cycloalkyl is unsubstituted or substituted once, twice or three times by halogen, —$NH_2$ or —OH, and R10 is as defined above, and Q is covalent bond, —($C_1$-$C_3$)-alkylene or —($C_3$-$C_6$)-cycloalkyl, on condition that at least one of the radicals $V_1$, $V_2$ or R5 is —($C_6$-$C_{14}$)-aryl or a mono- or bicyclic 4- to 15-membered heterocycle, in which aryl or heterocycle are unsubstituted or substituted once or twice by R8 or the radical -G-M.

3) The invention further relates to the compound of the formula I where
Z is —C(O)—,
R1 and R2 are identical or different and are independently of one another hydrogen atom or
—($C_1$-$C_4$)-alkyl, or R1 and R2 form together with the carbon atom to which they are respectively bonded
—($C_3$-$C_6$)-cycloalkyl, R3 and R4 are identical or different and are independently of one another
a covalent bond, —($CH_2$)$_m$— or —($C_1$-$C_3$)-alkylene-O—($C_0$-$C_3$)-alkylene-, in which
m is the integer 1, and in which the alkylene radical which is formed by —($CH_2$)$_m$— is unsubstituted or substituted once by —OH, $V_2$ is hydrogen atom,
$V_1$ and R5 are identical or different and are independently of one another
a) hydrogen atom,
b) —($C_6$-$C_{14}$)-aryl in which aryl is phenyl and is unsubstituted or substituted once or twice by R8 or the radical -G-M, or
c) a mono- or bicyclic 4- to 15-membered heterocycle in which heterocycle is a radical from the series benzodioxol, quinolinyl or pyridyl, in which the heterocycle is unsubstituted or substituted once, twice or three times by R8 or the radical -G-M, M is a) hydrogen atom,
b) —($C_6$-$C_{14}$)-aryl in which aryl is phenyl and is unsubstituted or substituted once or twice by R8, or
c) a mono- or bicyclic 4- to 15-membered heterocycle in which heterocycle is as defined above and in which the heterocycle is unsubstituted or substituted once, twice or three times by R8, R8 is halogen, —OH or —($C_1$-$C_4$)-alkyl or —O—($C_1$-$C_4$)-alkyl, G is covalent bond, —($C_0$-$C_3$)-alkylene-O—($C_0$-$C_3$)-alkylene- or —($C_0$-$C_3$)-alkylene-O—($C_2$-$C_4$)-alkenylene-, and Q is covalent bond or —($C_1$-$C_3$)-alkylene, on condition that at least one of the radicals $V_1$ or R5 is —($C_6$-$C_{14}$)-aryl or a mono- or bicyclic 4- to 15-membered heterocycle, in which aryl or heterocycle are unsubstituted or substituted once or twice by R8 or the radical -G-M.

4) The invention further relates to compounds of the formula I from the series 2-(3-(4-benzyloxybenzyl)-2-oxoimidazolidin-1-yl)-N-hydroxy-3-methylbutyramide, 2-(3-(4-benzyloxyphenyl)-2-oxoimidazolidin-1-yl)-N-hydroxy-3-methylbutyramide, 2-(3-(3-benzyloxybenzyl)-2-oxoimidazolidin-1-yl)-N-hydroxy-3-methylbutyramide, N-hydroxy-3-methyl-2-(2-oxo-3-(4-phenoxybenzyl)imidazolidin-1-yl)butyramide, 2-(3-(6-benzyloxypyridin-3-ylmethyl)-2-oxoimidazolidin-1-yl)-N-hydroxy-3-methylbutyramide, 2-(3-biphenyl-4-ylmethyl-2-oxoimidazolidin-1-yl)-N-hydroxy-3-methylbutyramide, 2-(3-benzyl-5-(4-methoxyphenyl)-2-oxoimidazolidin-1-yl)-N-hydroxy-3-methylbutyramide, N-hydroxy-2-(3-(4-hydroxybenzyl)-2-oxoimidazolidin-1-yl)-3-methylbutyramide, N-hydroxy-2-(3-(3-hydroxybenzyl)-2-oxoimidazolidin-1-yl)-3-methylbutyramide, N-hydroxy-3-methyl-2-{2-oxo-3-(4-(pyridin-4-ylmethoxy)benzyl)imidazolidin-1-yl}-butyramide with TFA, N-hydroxy-3-methyl-2-{2-oxo-3-(4-(pyridin-3-ylmethoxy)benzyl)imidazolidin-1-yl}-butyramide with TFA, N-hydroxy-3-methyl-2-{2-oxo-3-(4-(pyridin-2-ylmethoxy)benzyl)imidazolidin-1-yl}-butyramide with TFA, 2-(3-(4-but-2-ynyloxybenzyl)-2-oxoimidazolidin-1-yl)-N-hydroxy-3-methylbutyramide, N-hydroxy-3-methyl-2-{3-(4-(2-methylquinolin-4-yl-methoxy)benzyl)-2-oxoimidazolidin-1-yl}butyramide with TFA, 2-(3-benzyl-5-(4-methoxybenzyl)-2-oxoimidazolidin-1-yl)-N-hydroxy-3-methylbutyramide, 2-(3-(4-benzyloxybenzyl)-5-(4-methoxybenzyl)-2-oxoimidazolidin-1-yl)-N-hydroxy-3-methylbutyramide, N-hydroxy-2-(5-(4-methoxybenzyl)-3-methyl-2-oxoimidazolidin-1-yl)-3-methylbutyramide, 2-(5-benzo(1,3)dioxol-5-ylmethyl-3-(4-benzyloxybenzyl)-2-oxoimidazolidin-1-yl)-N-hydroxy-3-methylbutyramide, 2-(5-benzo(1,3)dioxol-5-ylmethyl-3-benzyl-2-oxoimidazolidin-1-yl)-N-hydroxy-3-methylbutyramide, 2-(5-(4-benzyloxybenzyl)-3-(4-methoxybenzyl)-1,1-dioxo-(1,2,5)thiadiazolidin-2-yl)-N-hydroxy-3-methylbutyramide or 2-(3-(4-benzyloxyphenyl)-2-oxo-(1,3)diazepan-1-yl)-N-hydroxy-3-methylbutyramide.

The term "—$(C_1-C_6)$-alkyl" means hydrocarbon radicals whose carbon chain is straight-chain or branched and comprises 1 to 6 carbon atoms, for example methyl, ethyl, propyl, isopropyl, butyl, isobutyl, tertiary butyl, pentyl, isopentyl, neopentyl, hexyl, 2,3-dimethylbutane or neohexyl.

The term "—$(CH_2)_o$— in which o is the number zero, 1, 2, 3, 4, 5 or 6" means when o is zero a covalent bond, o is 1 the methylene radical, o is 2 the ethylene radical, o is 3 propylene, o is 4 butenylene, o is 5 pentylene and o is 6 hexylene. The meanings of the term "—$(CH_2)_p$— in which p is the number zero, 1, 2, 3, 4, 5 or 6" are analogous to the term —$(CH_2)_o$—.

The term "—$(CH_2)_n$— in which n is the integer zero, 1, 2, 3, 4, 5 or 6" means when n is zero a covalent bond, n is 1 the methylene radical, n is 2 the ethylene radical, n is 3 propylene, n is 4 butenylene, n is 5 pentylene and n is 6 hexylene. The meanings of the term "—$(CH_2)_m$— in which m is the number 1, 2, 3, 4, 5 or 6" are analogous to the term —$(CH_2)_n$—.

The term "—$(C_0-C_3)$-alkylene-" means hydrocarbon radicals whose carbon chain is straight-chain or branched and comprises 1 to 3 carbon atoms, such as the radicals methylene, ethylene or propylene. The term "—$C_0$-alkylene-" means a covalent bond.

The term "—$(C_2-C_4)$-alkenylene" means hydrocarbon radicals whose carbon chain is straight-chain or branched and comprises 2 to 4 carbon atoms and have, depending on the chain length, 1 or 2 double bonds, for example ethenylene, propenylene, isopropenylene, isobutenylene or butenylene; the substituents on the double bond may, where the possibility exists in principle, be arranged in the E or Z configuration.

The term "halogen" means fluorine, chlorine, bromine or iodine.

The term "—$(C_3-C_6)$-cycloalkyl" means radicals such as compounds which are derived from 3- to 6-membered monocycles such as cyclopropyl, cyclobutyl, cyclopentyl or cyclohexyl.

The term "—$(C_1-C_3)$-perfluoroalkyl" means partly or completely fluorinated alkyl radicals which are derived from the following radicals such as —$CF_3$, —$CHF_2$, —$CH_2F$, —CHF—$CF_3$, —CHF—$CHF_2$, —CHF—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$,
—$CH_2$—CHF—$CF_3$, —$CH_2$—CHF—$CHF_2$, —$CH_2$—CHF—$CH_2F$, —$CH_2$—$CH_2$—$CF_3$, —$CH_2$—$CH_2$—$CHF_2$,
—$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —CHF—CHF—$CF_3$, —CHF—CHF—$CHF_2$, —CHF—CHF—$CH_2F$, —CHF—$CH_2$—$CF_3$, —CHF—$CH_2$—$CHF_2$, —CHF—$CH_2$—$CH_2F$, —CHF—$CF_2$—$CF_3$, —CHF—$CF_2$—$CHF_2$, —CHF—$CF_2$—$CH_2F$, —$CF_2$—CHF—$CF_3$, —$CF_2$—CHF—$CHF_2$, —$CF_2$—CHF—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

The term "—$(C_6-C_{14})$-aryl" means aromatic carbon radicals having 6 to 14 carbon atoms in the ring. —$(C_6-C_{14})$-Aryl radicals are for example phenyl, naphthyl, for example 1-naphthyl, 2-naphthyl, biphenylyl, for example 2-biphenylyl, 3-biphenylyl and 4-biphenylyl, anthryl or fluorenyl. Biphenylyl radicals, naphthyl radicals and, in particular, phenyl radicals are preferred aryl radicals.

The term "a mono- or bicyclic 4- to 15-membered heterocycle which comprises at least one carbon atom and one, two, three or four heteroatoms from the series nitrogen, sulfur or oxygen" or "Het" means radicals such as acridinyl, azetidinyl, benzimidazolyl, benzodioxol, benzodiazine, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, beta-carbolinyl, quinazolinyl, quinolinyl, 4H-quinolizinyl, quinoxalinyl, quinuclidinyl, chromanyl, chromenyl, decahydroquinolinyl, dihydrofuran, dithiazinyl, dithiazolly, fuaranyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyro-azolidinyl, pyrazolinyl, pyrazolyl, pyridazinyl, pryidooxazolyl, pyridoimidazolyl, pyridothiazolyl, pyridothiophenyl, pyridyl, pyrimidinyl, pyrrolidinyl, pyrrolinyl, pyrrolyl, tetrahydrofuranyl, tetrahydroisoquinolinyl, tetrahydroquinolinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, triazinyl, 1,2,3-triazolyl, 1,2,4-triazolyl, 1,2,5-triazolyl, 1,3,4-triazolyl and xanthenyl.

Preferred heterocycle radicals are benzodioxol, benzofuranyl, benzothiophenyl, 1,3-benzodioxolyl, benzimidazolyl, benzoxazolyl, benzothiazolyl, quinolinyl, chromanyl, isochromanyl, quinazolinyl, quinoxalinyl, furyl, imidazolyl, indazolyl, indolyl, isoquinolinyl, isoindolyl, isothiazolyl, isoxazolyl, oxazolyl, phthalazinyl, pteridinyl, purinyl, pyrazinyl, pyrazolyl, pyridazinyl, pyridoimidazolyl, pyridopyridinyl, pyridopyrimidinyl, pyridyl, pyrimidinyl, pyrrolyl, tetrazolyl, thiazolyl and thienyl.

Acidic or basic products of the compound of the formula I may be in the form of their salts or in free form. Pharmacologically acceptable salts are preferred, for example alkali metal or alkaline earth metal salts, or hydrochlorides, hydrobromides, sulfates, hemisulfates, all possible phosphates, and salts of amino acids, natural bases or carboxylic acids.

Physiologically tolerated salts are prepared from compounds of the formula I which are capable of salt formation, including their stereoisomeric forms, by method step d) in a manner known per se. The compounds of the formula I form stable alkali metal, alkaline earth metal or optionally substituted ammonium salts with basic reagents such as hydroxides, carbonates, bicarbonates, alcoholates, and ammonia or organic bases, for example trimethyl- or triethylamine, ethanolamine, diethanolamine or triethanolamine, trometamol or else basic amino acids, for instance lysine, ornithine or arginine. Where the compounds of the formula I have basic groups, stable acid addition salts can also be prepared with strong acids. Suitable for this purpose are both inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic, or TFA.

The invention further relates to a method for preparing the compound of the formula I and/or a stereoisomeric form of the compound of the formula I and/or a physiologically tolerated salt of the compound of the formula I, which comprises a) converting a compound of the formula II

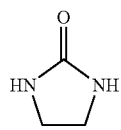

(II)

with a compound X-Q-R5 in which Q and R5 are defined as in the compound of the formula I, and X is a halogen, into a compound of the formula III

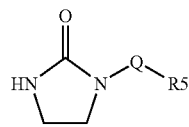

(III)

and converting with a compound of the formula IV

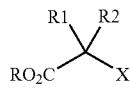

(IV)

in which R1 and R2 are defined as in formula I, X is a halogen, and R is a carboxyl protective group,
into a compound of the formula V

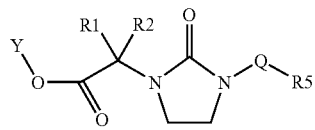

(V)

and subsequently converting the compound of the formula V into the hydroxamic acid, in which Y is NH—OH, of the formula I, or b) converting a compound of the formula VI

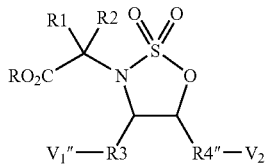

(VI)

in which R1, R2, R3 and V1 are defined as in formula I, and R is a carboxy protective group, with a compound $NH_2$-Q-R5 in which Q and R5 are defined as in the compound of the formula I, into a compound of the formula VII

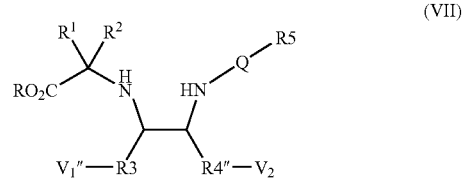

(VII)

and subsequently converting with $COCl_2$ or $SOCl_2$ into a compound of the formula VIII

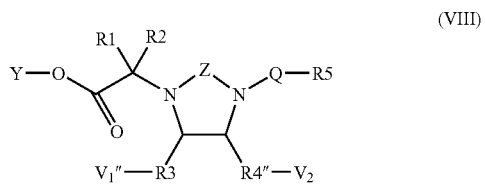

(VIII)

and subsequently converting the compound of the formula VIII into the hydroxamic acid, in which Y is NH—OH, of the formula I, or c) fractionating a compound of the formula I which has been prepared by method a) or b) and which, owing to its chemical structure, occurs in enantiomeric forms into the pure enantiomers by salt formation with enantiopure acids or bases, chromatography on chiral stationary phases or derivatization using chiral enantiopure compounds such as amino acids, separating the diastereomers obtained thus, and eliminating the chiral auxiliary groups, or d) either isolating in free form the compound of the formula I which has been prepared by methods a), b), or c) or, in the case where acidic or basic groups are present, converting into physiologically tolerated salts.

Syntheses of compounds of the formula III are described in the prior art, for example for Q=$CH_2$ and R5=2-chloropyridyl in J. Med. Chem. 1999, 42(12), 2227. Reaction with a halide of the formula X-Q-R5 proceeds in the presence of a base such as potassium carbonate, cesium carbonate, sodium hydride, lithium diisopropylamide or lithium bis(trimethylsilyl)amide.

Compounds of the formula V can be prepared from compounds of the formula III by deprotonation with a base such as lithium bis(trimethylsilyl)amide, lithium diisopropylamide, potassium carbonate, cesium carbonate or sodium hydride and alkylation with compounds of the formula IV, for example described in Bioorg. Med. Chem. Lett. 2002, 12(1), 25.

Compounds of the formula V are converted into the hydroxamic acid of the formula I by deprotection of the carboxyl function in a suitable way and conversion of the free carboxylic acid in analogy to the known methods as described in WO97/18194 or Tetrahedron Lett. 1992, 33(14), 1827. Suitable carboxyl protective groups for compounds of the formula IV are for example esters such as t-butyl, benzyl, isopropyl, ethyl or methyl esters. Cleavage thereof, and further suitable protective groups for the carboxyl function, are described in "Protective Groups in Organic Synthesis" T. W. Greene, P. G. M. Wuts, John Wiley & Sons, Inc., 1999, pages 369-431.

Compounds of the formula VI can be converted into compounds of the formula VII by reaction with amines of the type $NH_2$-Q-R5 in the presence of a base such as cesium carbonate, potassium carbonate, triethylamine, diisopropylethylamine. Instead of an addition base, this is also possible to employ the amine $NH_2$-Q-R5 in excess (greater than two mole equivalents) as described in Tetrahedron Lett. 1999, 40(43), 7687.

Procedures for converting compounds of the formula VII into compounds of the formula VIII are known. Thus, for example, this is possible for Z=CO by reaction with phosgene, triphosgene or carbonyldiimidazole, as described in J. Med. Chem. 1992, 35(5), 823. This is possible for $Z=SO_2$ by reacting compounds of the formula VII with $SO_2Cl_2$ as described in J. Org. Chem. 1987, 52(4), 479 or by reaction with $SOCl_2$ in analogy to Tetrahedron Lett. 1989, 30(29), 3873. Several methods known from the literature are available for the subsequent oxidation, as described in J. Med. Chem. 1981, 24(11), 1300 or Tetrahedron Lett. 2001, 42(8), 1433.

Compounds of the formula VIII can be converted in analogy to compounds of the formula V into hydroxamic acids of the formula I.

In process step c), the compound of the formula I is, if it occurs as mixture of diastereomers or enantiomers or results as mixtures thereof in the chosen synthesis, is separated into the pure stereoisomers, either by chromatography on an optionally chiral support material or, if the racemic compound of the formula I is capable of salt formation, by fractional crystallization of the diastereomeric salts formed with an optically active base or acid as auxiliary. Examples of suitable chiral stationary phases for thin-layer or column chromatographic separation of enantiomers are modified silica gel supports (called Pirkle phases) and high molecular weight carbohydrates such as triacetylcellulose. For analytical purposes, gas chromatographic methods on chiral stationary phases can also be used after appropriate derivatization known to the skilled worker. To separate enantiomers of the racemic carboxylic acids, diastereomeric salts differing in solubility are formed using an optically active, usually commercially available, base such as (−)-nicotine, (+)- and (−)-phenylethylamine, quinine bases, L-lysine or L- and D-arginine, the less soluble component is isolated as solid, the more soluble diastereomer is deposited from the mother liquor, and the pure enantiomers are obtained from the diastereomeric salts obtained in this way. It is possible in the same way in principle to convert the racemic compounds of the formula I containing a basic group such as an amino group with optically active acids such as (+)-camphor-10-sulfonic acid, D- and L-tartaric acid, D- and L-lactic acid and (+) and (−)-mandelic acid into the pure enantiomers. Chiral compounds containing alcohol or amine functions can also be converted with appropriately activated or, where appropriate, N-protected enantiopure amino acids into the corresponding esters or amides, or conversely chiral carboxylic acids can be converted with carboxyl-protected enantiopure amino acids into the amides or with enantiopure hydroxy carboxylic acids such as lactic acid into the corresponding chiral esters. The chirality of the amino acid or alcohol residue introduced in enantiopure form can then be utilized for separating the isomers by carrying out a separation of the diastereomers which are now present by crystallization or chromatography on suitable stationary phases, and then eliminating the included chiral moiety by suitable methods.

A further possibility with some of the compounds of the invention is to employ diastereomerically or enantiomerically pure starting materials to prepare the structures. It is thus possible where appropriate also to employ other or simplified processes for purifying the final products. These starting materials have previously been prepared enantiomerically or diastereomerically pure by processes known from the literature. This may mean in particular that in the synthesis of the basic structures either enantioselective methods are employed, or else a separation of enantiomers (or diastereomers) is carried out at an early stage of the synthesis and not just at the stage of the final products. It is likewise possible to achieve a simplification of the separations by a two-stage or multistage procedure.

Acidic or basic products of the compound of the formula I may be in the form of their salts or in free form. Pharmacologically acceptable salts are preferred, for example alkali metal or alkaline earth metal salts, or hydrochlorides, hydrobromides, sulfates, hemisulfates, all possible phosphates, and salts of amino acids, natural bases or carboxylic acids.

Physiologically tolerated salts are prepared from compounds of the formula I which are capable of salt formation, including their stereoisomeric forms, by method step d) in a manner known per se. The compounds of the formula I form stable alkali metal, alkaline earth metal or optionally substituted ammonium salts with basic reagents such as hydroxides, carbonates, bicarbonates, alcoholates, and ammonia or organic bases, for example trimethyl- or triethylamine, ethanolamine, diethanolamine or triethanolamine, trometamol or else basic amino acids, for instance lysine, ornithine or arginine. Where the compounds of the formula I have basic groups, stable acid addition salts can also be prepared with strong acids. Suitable for this purpose are both inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic, or TFA.

The invention also relates to medicaments having an effective content of at least one compound of the formula I and/or of a physiologically tolerated salt of the compound of the formula I and/or an optionally stereoisomeric form of the compound of the formula I, together with a pharmaceutically suitable and physiologically tolerated carrier, additive and/or other active substances and excipients.

Because of the pharmacological properties, the compounds of the invention are suitable for the selective prophylaxis and therapy of all disorders in the progression of which an enhanced activity of metalloproteinases such as aggrecanase or TNF-α are involved. These include degenerative joint disorders such as osteoarthroses, spondyloses, chondrolysis after joint trauma or prolonged joint immobilization after meniscus or patellar injuries or ligament tears. They also include connective tissue disorders such as collagenoses, periodontal disorders, wound-healing disturbances and chronic disorders of the locomotor system such as inflammatory, immunologically or metabolism-related acute and chronic arthritides, arthropathies, myalgias and disturbances of bone metabolism. The compounds of the formula I are also suitable for the treatment of ulceration, atherosclerosis and stenoses. The compounds of the formula I are furthermore suitable for the treatment of inflammations, cancers, tumor metastasis, cachexia, anorexia, heart failure and septic shock.

The term "osteoarthrosis" means a disorder which arises chiefly when there is a disparity between the strain and load capacity of the individual portions of joints and tissues of joints which is associated with an increasing destruction of cartilage and is chiefly not inflammatory. The main features of the pathology are damage to the articular cartilage such as fraying, demedullation or hyalinization, followed by reactive changes to the subchondral bone and capsular alterations.

The term "spondylosis" means an arthrosis of the vertebrae which is characterized by a non-inflammatory chondrolysis of the vertebrae and intervertebral disks.

The medicaments of the invention can be administered by oral, inhalational, rectal or transdermal administration or by subcutaneous, intraarticular, intraperitoneal or intravenous injection. Oral administration is preferred.

The invention also relates to a process for producing a medicament which comprises converting at least one compound of the formula I with a pharmaceutically suitable and physiologically tolerated carrier and, where appropriate, further suitable active substances, additives or excipients into a suitable dosage form.

Examples of suitable solid or pharmaceutical preparations are granules, powders, coated tablets, tablets, (micro)capsules, suppositories, syrups, oral solutions, suspensions, emulsions, drops or injectable solutions, and products with protracted release of active substance, in the production of which conventional aids such as carriers, disintegrants, binders, coating agents, swelling agents, glidants or lubricants, flavorings, sweeteners and solubilizers are used. Excipients which are frequently used and may be mentioned are magnesium carbonate, titanium dioxide, lactose, mannitol and other sugars, talc, milk protein, gelatin, starch, cellulose and its derivatives, animal and vegetable oils such as fish liver oil, sunflower, peanut or sesame oil, polyethylene glycol and solvents such as, for example, sterile water and monohydric or polyhydric alcohols such as glycerol.

The pharmaceutical products are preferably produced and administered in dosage units, each unit comprising as active ingredient a particular dose of the compound of the invention of the formula I. In the case of solid dosage units such as tablets, capsules, coated tablets or suppositories, this dose can be up to about 1000 mg, but preferably about 50 to 300 mg, and in the case of solutions or injection in ampoule form up to about 300 mg, but preferably about 10 to 100 mg.

The daily doses indicated for the treatment of an adult patient weighing about 70 kg are from about 20 mg to 1000 mg of active substance, preferably about 100 mg to 500 mg, depending on the activity of the compound of the formula I. However, in some circumstances, higher or lower daily doses may also be appropriate. The daily dose may be administered both by administration once a day in the form of a single dosage unit or else a plurality of smaller dosage units, and by administration more than once a day in divided doses at defined intervals.

Products are usually characterized by mass spectroscopic methods (FAB-, ESI-MS), with the main peak or the two main peaks being indicated in each case, and by their retention time ($R_t$) in LC/MS (the method used is noted in each case). Temperatures are stated in degrees Celsius, RT means room temperature (22° C. to 26° C.). Abbreviations used are either explained or correspond to the usual conventions.

The invention is explained in detail below by means of examples.

EXAMPLES

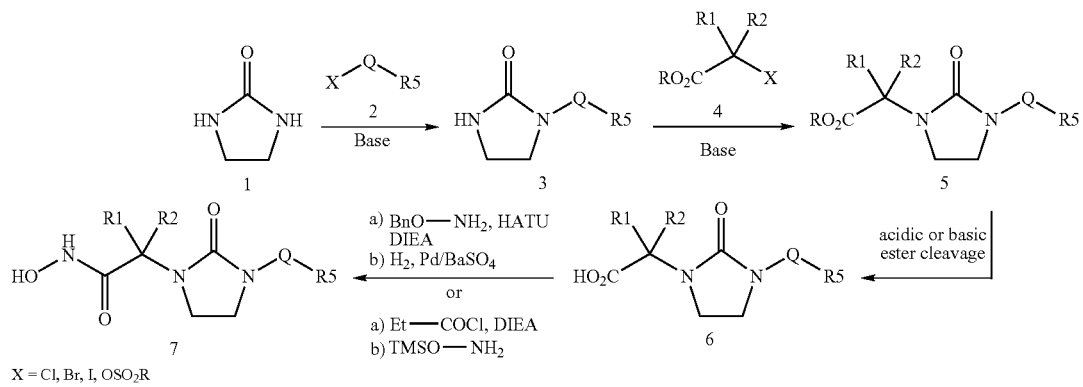

Scheme 1

X = Cl, Br, I, OSO$_2$R 1.1 1-(4-Benzyloxybenzyl)imidazolidin-2-one (3)

Imidazolidin-2-one (2.0 g; 23.23 mmol) was dissolved in dimethyl sulfoxide (DMSO; 30 ml). Potassium carbonate (3.10 g; 23.23 mmol), potassium iodide (0.95 g; 5.80 mmol) and 4-benzyloxybenzyl chloride (5.4 g; 23.23 mmol) were added thereto. The mixture was heated at 100° C. for 3 hours (h). Cooling to RT was followed by partition between water (100 ml) and ethyl acetate (EtOAc, 100 ml). The phases were separated and the aqueous phase was extracted with EtOAc (3×; 30 ml). The combined organic phases were washed with saturated NaCl solution (80 ml) and dried over MgSO$_4$. The solvent was removed under reduced pressure in a rotary evaporator. Trituration of the residue with EtOAc (10 ml) triturated resulted in 1-(4-benzyloxybenzyl)-imidazolidin-2-one (2.10 g; 7.43 mmol). MS: 283.15 (M+H); $R_t$: 1.38 min (method: gradient 0 min 90% H$_2$O (0.05% TFA) 1.9 min 95% acetonitrile, 95% acetonitrile to 2.4 min, 10% acetonitrile 2.45 min; flow rate 1 ml/min; column 0.4 μL (YMC J'sphere ODS H80 20X2 1.4μ); 30° C.)

1.2 Ethyl 2-(3-(4-benzyloxybenzyl)-2-oxoimidazolidin-1-yl)-3-methylbutyrate (5)

1-(4-Benzyloxybenzyl)imidazolidin-2-one (1.0 g; 3.54 mmol) was dissolved in dimethylformamide (DMF, 10 ml). NaH (60% in mineral oil; 0.085 g; 3.54 mol) was added, and the mixture was heated at 40° C. for 1 h. Then ethyl 2-bromoisovalerate (0.74 g; 3.54 mmol) were added, and heating was continued at 60° C. for 4 h. The reaction was stopped by slow addition of water (1 ml). The solvent was removed under reduced pressure, and the residue was partitioned between water (50 ml) and EtOAc (50 ml). Dilute HCl was added until the pH of the aqueous phase was about 4. The phases were then separated, and the aqueous phase was extracted with EtOAc (2×; 30 ml). The combined organic phases were dried over MgSO$_4$. The solvent was removed under reduced pressure. Purification of the residue by column chromatography on silica gel (SiO$_2$) resulted in ethyl 2-(3-(4-benzyloxybenzyl)-2-oxoimidazolidin-1-yl)-3-methylbutyrate (0.38 g; 0.92 mmol). MS: 411.15 (M+H); R$_t$: 1.87 min (method: gradient 0 min 90% H$_2$O (0.05% TFA) 1.9 min 95% acetonitrile, 95% acetonitrile to 2.4 min, 10% acetonitrile 2.45 min; flow rate 1 ml/min; column 0.4 µL (YMC J'sphere ODS H80 20X2 1.4µ); 30° C.)

1.3 2-(3-(4-Benzyloxybenzyl)-2-oxoimidazolidin-1-yl)-3-methylbutyric acid (6)

Ethyl 2-(3-(4-benzyloxybenzyl)-2-oxoimidazolidin-1-yl)-3-methylbutyrate (0.330 g; 0.80 mmol) was dissolved in methanol (MeOH; 6 ml). NaOH solution (1N; 3 ml) as added, and the mixture was stirred at RT for 3 h. The solvent was removed under reduced pressure, and saturated NaH$_2$PO$_4$ solution (2 ml) was added to he residue. The solid was filtered off with suction and dried under reduced pressure at 60° C. to result in 2-(3-(4-benzyloxybenzyl)-2-oxoimidazolidin-1-yl)-3-methylbutyric acid (0.25 g; 0.66 mmol). MS: 383.10 (M+H); R$_t$: 1.57 min (method: gradient 0 min 90% H$_2$O (0.05% TFA) 1.9 min 95% acetonitrile, 95% acetonitrile to 2.4 min, 10% acetonitrile 2.45 min; flow rate 1 ml/min; column 0.4 µL (YMC J'sphere ODS H80 20X2 1.4µ); 30° C.)

1.4 2-(3-(4-Benzyloxybenzyl)-2-oxoimidazolidin-1-yl)-N-hydroxy-3-methylbutyramide (7)

2-(3-(4-Benzyloxybenzyl)-2-oxoimidazolidin-1-yl)-3-methylbutyric acid (50 mg; 0.13 mmol) was dissolved in tetrahydrofuran (THF; 2 ml). At 0° C., diisopropylethylamine (DIEA; 69 µl; 0.39 mmol) and ethyl chloroformate (25 µl; 0.26 mmol) were successively added. The mixture was allowed to reach RT from 0° C. over the course of 2 h, and then O-trimethylsilylhydroxylamine (50 µl; 0.65 mmol) was added. Stirring at RT for a further 3 h was followed by partitioning between dilute HCl (10 ml) and EtOAc (10 ml). The phases were separated and the aqueous phase was extracted with EtOAc (3×; 5 ml). The combined organic phases were dried over MgSO$_4$. The solvent was removed under reduced pressure. Trituration of the residue with EtOAc (2 ml) resulted in 2-(3-(4-benzyloxybenzyl)-2-oxoimidazolidin-1-yl)-N-hydroxy-3-methylbutyramide (25 mg; 0.06 mmol). MS: 398.15 (M+H); R$_t$: 1.30 min (method: gradient 0 min 96% H$_2$O (0.05% TFA) 2.0 min 95% acetonitrile, 95% acetonitrile to 2.4 min, 4% acetonitrile 2.45 min; flow rate 1 ml/min; column 0.4 µL (YMC J'sphere ODS H80 20X2 1.4µ); 30° C.)

Scheme 2

2.1 N-1-(4-Benzyloxyphenyl)ethane-1,2-diamine hydrochloride (10)

4-Benzyloxyaniline hydrochloride (10.0 g; 42.42 mmol) was dissolved in diethylene glycol monomethyl ether (40 ml). 2-Oxazolidone (4.43 g; 50.90 mmol) was added thereto, and the mixture was heated at 180° C. for 6 h. After cooling to RT, the solid was filtered off with suction. Washing with diethyl ether (Et$_2$O) resulted in N-1-(4-benzyloxyphenyl)ethane-1,2-diamine hydrochloride (3.50 g; 12.55 mmol). MS: 243.15 (M$_{free\ base}$+H); R$_t$: 0.96 min (method: gradient 0 min 90% H$_2$O (0.05% TFA) 1.9 min 95% acetonitrile, 95% acetonitrile to 2.4 min, 10% acetonitrile 2.45 min; flow rate 1 ml/min; column 0.4 µL (YMC J'sphere ODS H80 20X2 1.4µ); 30° C.)

2.2 Ethyl 2-(2-(4-benzyloxyphenylamino)ethylamino)-3-methylbutyrate (11)

N-1-(4-Benzyloxyphenyl)ethane-1,2-diamine hydrochloride (1.7 g; 6.09 mmol) was dissolved in DMF (15 ml). The solution was heated to 50° C., and triethylamine (NEt$_3$; 2.55 ml) was added thereto. Then ethyl-2-bromoisovalerate (1.66 g; 7.92 mmol) was added and the mixture was heated at 100° C. for 3 h. The solvent was removed under reduced pressure. Purification of the residue by column chromatography (SiO$_2$) resulted in ethyl 2-(2-(4-benzyloxyphenylamino)ethylamino)-3-methylbutyrate (0.30 g; 0.809 mmol). MS: 371.20 (M+H); R$_t$: 1.29 min (method: gradient 0 min 90% H$_2$O (0.05% TFA) 1.9 min 95% acetonitrile, 95% acetonitrile to 2.4 min, 10% acetonitrile 2.45 min; flow rate 1 ml/min; column 0.4 µL (YMC J'sphere ODS H80 20X2 1.4µ); 30° C.)

2.3 Ethyl 2-(3-(4-benzyloxyphenyl)-2-oxoimidazolidin-1-yl)-3-methylbutyrate (12)

Ethyl 2-(2-(4-benzyloxyphenylamino)ethylamino)-3-methylbutyrate (100 mg; 0.27 mmol) was dissolved in toluene (5 ml) and cooled to 0° C. DIEA (141 μl; 0.81 mmol) and phosgene (20% strength in toluene; 202 μl; 0.40 mmol) were added thereto. The mixture was allowed to reach RT over the course of 3 h, and then the solvent was removed under reduced pressure. The residue was partitioned between water (10 ml) and EtOAc (10 ml). The phases were separated and the aqueous phase was extracted with EtOAc (2×; 5 ml). The combined organic phases were dried over $MgSO_4$. After removal of the solvent whilst under reduced pressure, ethyl 2-(3-(4-benzyloxyphenyl)-2-oxoimidazolidin-1-yl)-3-methylbutyrate (90 mg; 0.22 mmol) was obtained. MS: 397.15 (M+H); $R_t$: 1.90 min (method: gradient 0 min 90% $H_2O$ (0.05% TFA) 1.9 min 95% acetonitrile, 95% acetonitrile to 2.4 min, 10% acetonitrile 2.45 min; flow rate 1 ml/min; column 0.4 μL (YMC J'sphere ODS H80 20X2 1.4μ); 30° C.)

2.4 2-(3-(4-Benzyloxyphenyl)-2-oxoimidazolidin-1-yl)-3-methylbutyric acid (13)

Ethyl 2-(3-(4-benzyloxyphenyl)-2-oxoimidazolidin-1-yl)-3-methylbutyrate (110 mg; 0.27 mmol) was dissolved in methanol (3 ml) at 0° C. Then sodium hydroxide solution (1N, 1.5 ml) was added, and the reaction mixture was stirred for 4 h during which it was allowed slowly to reach RT. The methanol was removed in a rotary evaporator, and the remaining solution was neutralized with saturated $NaH_2PO_4$ solution. The precipitated 2-(3-(4-benzyloxyphenyl)-2-oxoimidazolidin-1-yl)-3-methylbutyric acid (91 mg, 0.25 mmol) was filtered off with suction. MS: 369.20 (M+H); $R_t$: 1.58 min (method: gradient 0 min 90% $H_2O$ (0.05% TFA) 1.9 min 95% acetonitrile, 95% acetonitrile to 2.4 min, 10% acetonitrile 2.45 min; flow rate 1 ml/min; column 0.4 μL (YMC J'sphere ODS H80 20X2 1.4μ); 30° C.)

2.5 2-(3-(4-Benzyloxyphenyl)-2-oxoimidazolidin-1-yl)-N-hydroxy-3-methylbutyramide (14)

2-(3-(4-Benzyloxyphenyl)-2-oxoimidazolidin-1-yl)-3-methylbutyric acid (66 mg; 0.18 mmol) was dissolved in THF (2 ml). At 0° C., diisopropylethylamine (DIEA; 124 μl; 0.71 mmol) and ethyl chloroformate (51 μl; 0.53 mmol) were successively added. The mixture was allowed to reach RT from 0° C. over the course of 2 h and then O-trimethylsilylhydroxylamine (80.43 μl; 1.07 mmol) was added. Stirring at RT for a further 3 h was followed by partitioning between dilute HCl (10 ml) and EtOAc (10 ml). The phases were separated and the aqueous phase was extracted with EtOAc (3×; 5 ml). The combined organic phases were dried over $MgSO_4$. The solvent was removed under reduced pressure. Trituration of the residue with EtOAc (2 ml) resulted in 2-(3-(4-benzyloxyphenyl)-2-oxoimidazolidin-1-yl)-N-hydroxy-3-methylbutyramide (22 mg; 0.06 mmol). MS: 384.25 (M+H); $R_t$: 1.94 min (method: gradient acetonitrile+0.08% formic acid:$H_2O$+0.1% formic acid from 5:95 (0 min) to 95:5 (2.5 min) to 95:5 (3 min); flow rate 1.3 ml/min; column YMC Jsphere 33*2.1)

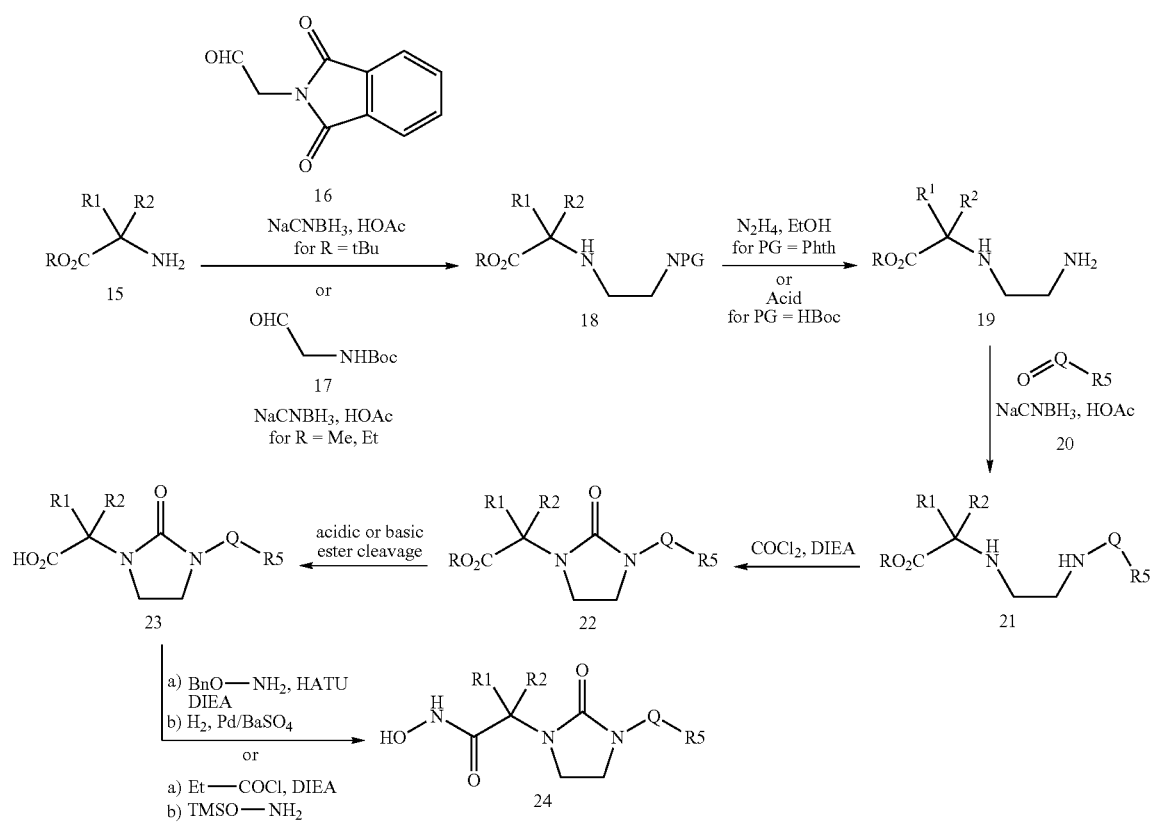

Scheme 3

3.1 t-Butyl 2-(2-(1,3-dioxo-1,3-dihydroisoindol-2-yl) ethylamino)-3-methylbutyrate (18)

(R)-Valine t-butyl ester (4.9 g; 28.28 mmol) was dissolved in methanol (100 ml). Acetic acid (1.62 ml; 28.28 mmol) and (1,3-dioxo-1,3-dihydroisoindol-2-yl)-acetaldehyde (5.40 g; 28.28 mmol) were added thereto. Then, sodium cyanoborohydride (1.95 g; 31.11 mmol) dissolved in THF (20 ml) was added. The mixture was stirred at RT for 6 h and then saturated NaHCO$_3$ solution (200 ml) was added. Methanol was removed under reduced pressure, and the residue was extracted with EtOAc (3×; 100 ml). The combined organic phases were dried over MgSO$_4$. Removal of the solvent under reduced pressure and purification of the residue by column chromatography (SiO') resulted in t-butyl (R)-2-(2-(1,3-dioxo-1,3-dihydroisoindol-2-yl)ethylamino)-3-methylbutyrate (6.60 g; 19.05 mmol). MS: 347.20 (M+H); R$_t$: 1.02 min (method: gradient 0 min 96% H$_2$O (0.05% TFA) 2.0 min 95% acetonitrile, 95% acetonitrile to 2.4 min, 4% acetonitrile 2.45 min; flow rate 1 ml/min; column 0.4 μL (YMC J'sphere ODS H80 20X2 1.4μ); 30° C.)

3.2 t-Butyl 2-(2-aminoethylamino)-3-methylbutyrate (19)

t-Butyl (R)-2-(2-(1,3-dioxo-1,3-dihydroisoindol-2-yl) ethylamino)-3-methylbutyrate (6.60 g; 19.05 mmol) was dissolved in ethanol (100 ml). Hydrazine hydrate (4.62 ml; 95.25 mmol) was added, and the reaction mixture was heated under reflux for 2 h. The solid was filtered off with suction through kieselguhr and washed with ethanol (100 ml). The solvent was removed and the residue was partitioned between saturated NaHCO$_3$ solution (150 ml) and CH$_2$Cl$_2$ (150 ml). The phases were separated and the aqueous phase was extracted with CH$_2$Cl$_2$ (2×; 100 ml). The combined organic phases were dried over MgSO$_4$. Removal of the solvent under reduced pressure resulted in t-butyl (R)-2-(2-aminoethylamino)-3-methylbutyrate (4.60 g; 19.05 mmol). MS: 217.25 (M+H); R$_t$: 0.69 min (method: gradient 0 min 96% H$_2$O (0.05% TFA) 2.0 min 95% acetonitrile, 95% acetonitrile to 2.4 min, 4% acetonitrile 2.45 min; flow rate 1 ml/min; column 0.4 μL (YMC J'sphere ODS H80 20X2 1.4μ); 30° C.)

3.3 t-Butyl 2-(2-(3-benzyloxybenzylamino)ethylamino)-3-methylbutyrate (21)

t-Butyl (R)-2-(2-aminoethylamino)-3-methylbutyrate (100 mg; 0.46 mmol) was dissolved in methanol (2 ml). Acetic acid (8 μl; 0.14 mmol), 3-benzyloxybenzaldehyde (98 mg; 0.46 mmol) and sodium cyanoborohydride (32 mg; 0.50 mmol) were added. Stirring at RT for 6 h was followed by partitioning between saturated NaHCO$_3$ solution (8 ml) and CH$_2$Cl$_2$ (8 ml). The phases were separated, and the aqueous phase was extracted with CH$_2$Cl$_2$ (2×; 5 ml). The combined organic phases were dried over MgSO$_4$, and the solvent was removed under reduced pressure. Purification by preparative HPLC afforded t-butyl (R)-2-(2-(3-benzyloxybenzylamino) ethylamine)-3-methylbutyrate (155 mg; 0.37 mmol) MS: 413.25 (M+H); R$_t$: 1.11 min (method: gradient 0 min 96% H$_2$O (0.05% TFA) 2.0 min 95% acetonitrile, 95% acetonitrile to 2.4 min, 4% acetonitrile 2.45 min; column 0.4 μL (YMC J'sphere ODS H80 20X2 1.4μ); 30° C.)

3.4 t-Butyl 2-(3-(3-benzyloxybenzyl)-2-oxoimidazolidin-1-yl)-3-methylbutyrate (22)

t-Butyl (R)-2-(2-(3-benzyloxybenzylamino)ethylamino)-3-methylbutyrate (155 mg; 0.37 mmol) was dissolved in toluene (5 ml) and cooled to 0° C. NaOH (1N; 5 ml; 5 mmol) was added, as was phosgene (20% in toluene; 0.37 ml; 0.75 mmol). The mixture was stirred at 0° C. for 6 h, the phases were separated, and the aqueous phase was extracted with CH$_2$Cl$_2$ (2×; 5 ml). The combined organic phases were dried over MgSO$_4$, and the solvents were removed under reduced pressure. Purification of the residue by column chromatography (SiO$_2$) resulted in t-butyl (R)-2-(3-(3-benzyloxybenzyl)-2-oxoimidazolidin-1-yl)-3-methylbutyrate (102 mg; 0.23 mmol). MS: 439.25 (M+H); R$_t$: 2.12 min (method: gradient 0 min 96% H$_2$O (0.05% TFA) 2.0 min 95% acetonitrile, 95% acetonitrile to 2.4 min, 4% acetonitrile 2.45 min; flow rate 1 ml/min; column 0.4 μL (YMC J'sphere ODS H80 20X2 1.4μ); 30° C.)

3.5 2-(3-(3-Benzyloxybenzyl)-2-oxoimidazolidin-1-yl)-N-hydroxy-3-methylbutyramide (24)

t-Butyl (R)-2-(3-(3-benzyloxybenzyl)-2-oxoimidazolidin-1-yl)-3-methylbutyrate (102 mg; 0.23 mmol) was dissolved in CH$_2$Cl$_2$ (2 ml) and cooled to 0° C. Trifluoroacetic acid (TFA; 1 ml) was added, and the mixture was stirred for 2 h. The solvents were removed under reduced pressure, and the residue was taken up in tetrahydrofuran (THF; 2 ml). DIEA (0.16 ml; 0.93 mmol) and ethyl chloroformate (67 μl; 0.69 mmol) were added. After stirring at RT for 2 h, O-trimethylsilylhydroxylamine (0.10 ml; 1.39 mmol) was added. The mixture was stirred for 15 h, HCl (6N, 0.30 ml) was added, and then the solvents were removed under reduced pressure. Purification of the residue by preparative HPLC resulted in (R)-2-(3-(3-benzyloxybenzyl)-2-oxoimidazolidin-1-yl)-N-hydroxy-3-methylbutyramide (8 mg, 0.02 mmol). MS: 398.15 (M+H); R$_t$: 1.46 min (method: gradient 0 min 96% H$_2$O (0.05% TFA) 2.0 min 95% acetonitrile, 95% acetonitrile to 2.4 min, 4% acetonitrile 2.45 min; flow rate 1 ml/min; column 0.4 μL (YMC J'sphere ODS H80 20X2 1.4μ); 30° C.)

Scheme 4

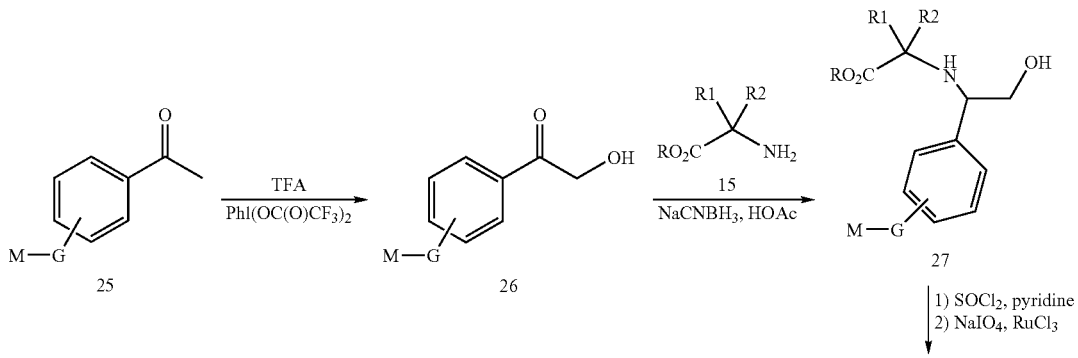

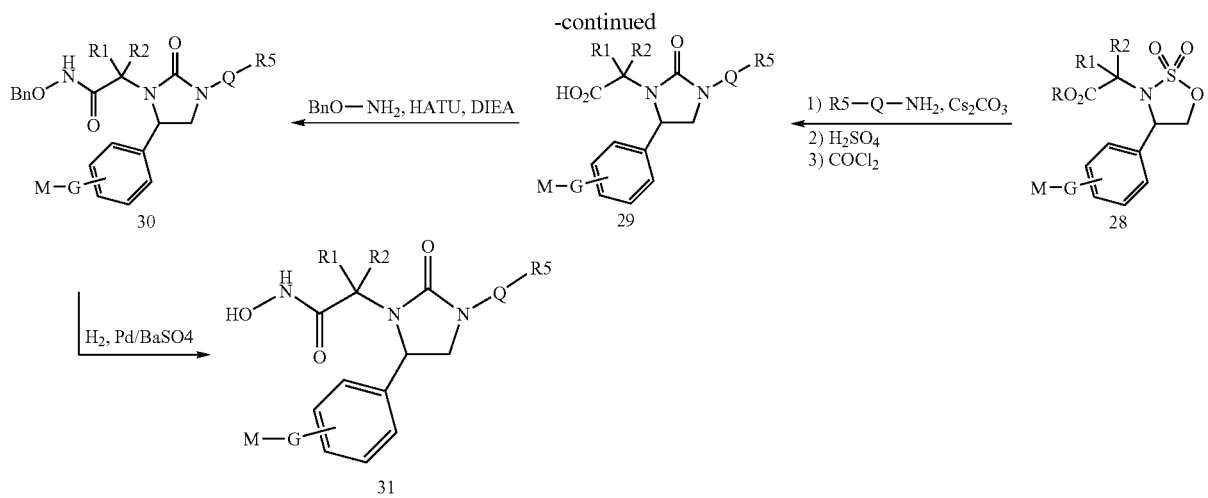

4.1 2-Hydroxy-1-(4-methoxyphenyl)ethanone (26)

4-Methoxyacetophenone (10 g; 66.59 mmol) was added to a solution of acetonitrile (350 ml), water (70 ml) and trifluoroacetic acid (TFA) (10.26 ml; 133.20 mmol). Then (bis(trifluoroacetoxy)iodo)benzene was added, and the reaction mixture was heated under reflux for 3 h. The acetonitrile was then stripped off in a rotary evaporator, and the reaction mixture was partitioned in $NaHCO_3$ solution/$CH_2Cl_2$. After extraction with $CH_2Cl_2$ (2×), the combined organic phases were dried over $MgSO_4$, and the solvent was removed in a rotary evaporator. Purification by column chromatography ($CH_2Cl_2$/MeOH 50:1) resulted in 2-hydroxy-1-(4-methoxyphenyl)ethanone (6.0 g; 36.1 mmol). MS: 167.15 (M+H); $R_t$: 0.83 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 μL (YMC J'sphere ODS H80 20X2 1.4μ); 30° C.)

4.2 t-Butyl 2-(2-hydroxy-1-(4-methoxyphenyl)ethylamino)-3-methylbutyrate (27)

Valine t-butyl ester hydrochloride (3.85 g; 18.38 mmol) was partitioned in 1N NaOH/$CH_2Cl_2$ and extracted with $CH_2Cl_2$ (2×), and the combined organic phases were dried over $MgSO_4$. After concentration in a rotary evaporator, the free amine obtained in this way was taken up in 1,2-dichloroethane (30 ml). Then, 2-hydroxy-1-(4-methoxyphenyl)ethanone (2.35 g; 14.14 mmol) and acetic acid (0.48 ml; 8.48 mmol) were added. The mixture was stirred at RT for 1 h and then $NaBH(OAc)_3$ (3.89 g; 18.38 mmol) was added, and stirring was continued at RT for 4 h. The reaction mixture was partitioned in $NaHCO_3$ solution/$CH_2Cl_2$ and extracted with $CH_2Cl_2$ (2×). The combined organic phases were dried over $MgSO_4$, and the solvent was removed in a rotary evaporator. Purification by chromatography resulted in t-Butyl 2-(2-hydroxy-1-(4-methoxyphenyl)-ethylamino)-3-methylbutyrate (2.5 g; 7.73 mmol). MS: 324.20 (M+H); $R_t$: 1.07 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 μL (YMC J'sphere ODS H80 20X2 1.4μ); 30° C.)

4.3 t-Butyl 2-(4-(4-methoxyphenyl)-2,2-dioxo-(1,2,3)oxathiazolidin-3-yl)-3-methylbutyrate (28)

t-Butyl 2-(2-hydroxy-1-(4-methoxyphenyl)ethylamino)-3-methylbutyrate (2.5 g; 7.73 mmol) was introduced into $CH_2Cl_2$ (200 ml), and the solution was cooled to −78° C. Addition of pyridine (3.12 ml; 38.65 mmol) was followed by slow dropwise addition of thionyl chloride (0.67 ml; 9.27 mmol). The reaction mixture was stirred for 1 h, during which the temperature was allowed to rise to 0° C. The reaction mixture was partitioned between aqueous 1% strength HCl/$CH_2Cl_2$ and extracted with $CH_2Cl_2$ (2×). The combined organic phases were washed with saturated $NaHCO_3$ solution and dried over $MgSO_4$, and the solvent was removed in a rotary evaporator. The residue was taken up in acetonitrile (20 ml) and cooled to 0° C. Then $NaIO_4$ (1.82 g; 8.5 mmol), $RuCl_3 \cdot H_2O$ (14.43 mg; 0.077 mmol) and water (20 ml) were added. The reaction mixture was stirred at 0° C. for 5 minutes and then at RT for a further 20 minutes. It was then partitioned between saturated $NaHCO_3$ solution/$CH_2Cl_2$ and extracted with $CH_2Cl_2$ (2×). The combined organic phases were washed with saturated $NaHCO_3$ and dried over $MgSO_4$, and the solvent was removed in a rotary evaporator. Purification by chromatography resulted in t-butyl 2-(4-(4-methoxyphenyl)-2,2-dioxo-(1,2,3)oxathiazolidin-3-yl)-3-methylbutyrate (2.5 g; 6.48 mmol). MS: 403.15 (M+$NH_4^+$); $R_t$: 1.82 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 μL (YMC J'sphere ODS H80 20X2 1.4μ); 30° C.).

4.4 2-(3-Benzyl-5-(4-methoxyphenyl)-2-oxoimidazolidin-1-yl)-3-methylbutyric acid (29)

t-Butyl 2-(4-(4-methoxyphenyl)-2,2-dioxo-(1,2,3)oxathiazolidin-3-yl)-3-methylbutyrate (0.30 g; 0.778 mmol) was introduced into acetonitrile (5 ml). Benzylamine (0.10 g; 0.93 mmol) and $Cs_2CO_3$ (0.50 g; 1.55 mmol) were added thereto, and the reaction mixture was stirred at 55° C. for 5 h. It was then filtered through kieselguhr, and the residue was washed with a solution of methanol (3%) in acetonitrile. The filtrate was concentrated in a rotary evaporator, and the residue was taken up in dioxane (10 ml) and concentrated aqueous $H_2SO_4$ (10 ml). The mixture was stirred at 70° C. for 2 h and then evaporated to dryness in a rotary evaporator. The residue was taken up in toluene, and 1N NaOH (10 ml) was added. After the reaction mixture had been cooled to 0° C., phosgene (20% in toluene; 0.58 ml; 1.16 mmol) was slowly added dropwise. The mixture was then stirred at 0° C. for 2 h. The reaction mixture was adjusted to pH 1-2 with dilute aqueous HCl, mixed with EtOAc and extracted with EtOAc (2×). The combined organic phases were dried over $MgSO_4$, and the solvent was removed in a rotary evaporator. Purification by column chromatography ($CH_2Cl_2$/MeOH, gradient) resulted in 2-(3-benzyl-5-(4-methoxyphenyl)-2-oxoimidazolidin-1-yl)-3-methylbutyric acid (0.15 g; 0.39 mmol). MS: 383.15 (M+H); $R_t$: 1.52 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 μL (YMC J'sphere ODS H80 20X2 1.4μ); 30° C.)

4.5 2-(3-Benzyl-5-(4-methoxyphenyl)-2-oxoimidazolidin-1-yl)-N-benzyloxy-3-methylbutyramide (30)

2-(3-Benzyl-5-(4-methoxyphenyl)-2-oxoimidazolidin-1-yl)-3-methylbutyric acid (150 mg; 0.39 mmol) was introduced into DMF (10 ml) and cooled to 0° C. Then N,N-diisopropylethylamine (202 mg; 1.56 mmol), O-benzylhydroxylamine hydrochloride (125 mg, 0.78 mmol) and O-(7-azabenzotriazol-1-yl)-N,N,N',N'-tetramethyluronium hexafluorophosphate (HATU; 223 mg; 0.58 mmol) were added, and the mixture was stirred at 0° C. for 2 h. The reaction solution was then concentrated and partitioned between dilute HCl solution/EtOAc and extracted with EtOAc (2×). The combined organic phases were dried over $MgSO_4$, and the solvent was removed in a rotary evaporator. Purification by chromatography resulted in 2-(3-benzyl-5-(4-methoxyphenyl)-2-oxoimidazolidin-1-yl)-N-benzyloxy-3-methylbutyramide (116 mg; 0.24 mmol). MS: 488.25 (M+H); $R_t$: 3.50 min (method: gradient 95% $H_2O$ (0.05% TFA) to 95% acetonitrile over 3.5 min, 95% acetonitrile for 1.0 min, 5% acetonitrile 1.0 min; flow rate 0.5 ml/min; column 1 μL (Merck Purospher 5μ 2×55 mm); 30° C.)

4.6 2-(3-Benzyl-5-(4-methoxyphenyl)-2-oxoimidazolidin-1-yl)-N-hydroxy-3-methylbutyramide (31)

2-(3-Benzyl-5-(4-methoxyphenyl)-2-oxoimidazolidin-1-yl)-N-benzyloxy-3-methylbutyramide (120 mg; 0.24 mmol) was introduced into methanol (10 ml), and Pd/$BaSO_4$ (50 mg) was added. The mixture was hydrogenated with $H_2$ (1 atm) at RT for 4 h. The reaction mixture was then filtered through kieselguhr, the residue was washed with methanol, and the filtrate was concentrated in a rotary evaporator. Purification by preparative HPLC resulted in 2-(3-benzyl-5-(4-methoxyphenyl)-2-oxoimidazolidin-1-yl)-N-hydroxy-3-methylbutyramide (60 mg, 0.15 mmol). MS: 398.15 (M+H); $R_t$: 1.31 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 μL (YMC J'sphere ODS H80 20X2 1.4μ); 30° C.)

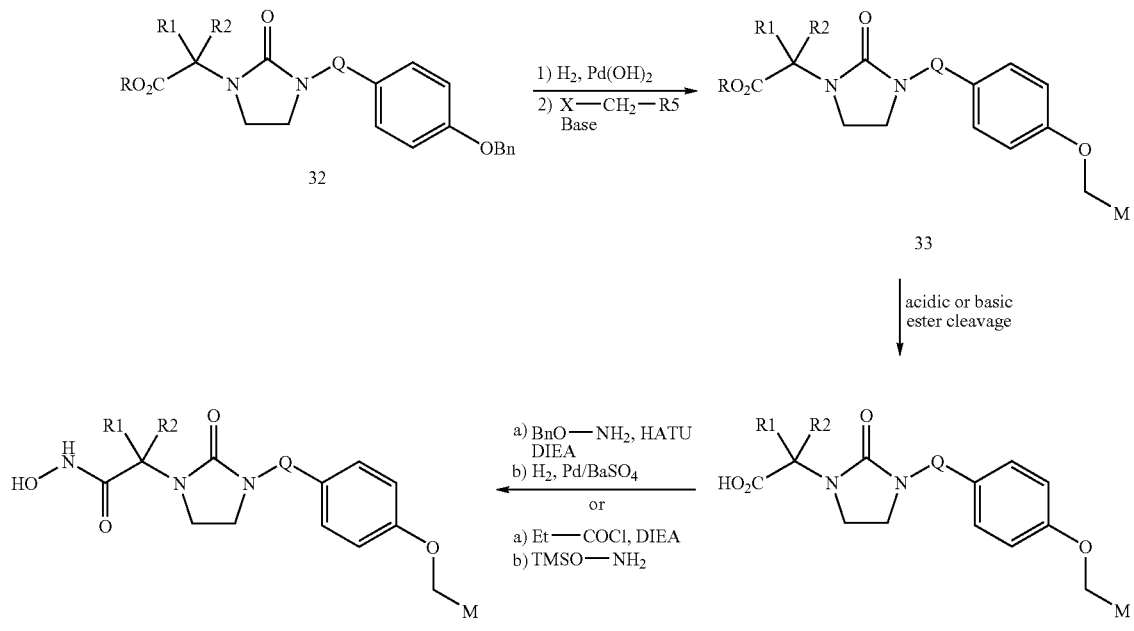

Scheme 5

5.1 Ethyl 2-(3-(4-hydroxybenzyl)-2-oxoimidazolidin-1-yl)-3-methylbutyrate (32)

Ethyl 2-(3-(4-benzyloxybenzyl)-2-oxoimidazolidin-1-yl)-3-methylbutyrate (400 mg; 0.97 mmol) was dissolved in ethanol (20 ml). $Pd(OH)_2$ (100 mg; 0.71 mmol) was added thereto, and hydrogenation was carried out under about 1 atm. of hydrogen for 3 h. The catalyst was filtered off through kieselguhr and washed with ethanol (2×; 20 ml). The solvent was removed under reduced pressure. Purification of the residue by column chromatography ($SiO_2$) resulted in ethyl 2-(3-(4-hydroxybenzyl)-2-oxoimidazolidin-1-yl)-3-methylbutyrate (300 mg; 0.94 mmol). MS: 321.35 (M+H); $R_t$: 1.24 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 μL (YMC J'sphere ODS H80 20X2 1.4μ); 30° C.)

5.2 Ethyl 3-methyl-2-{2-oxo-3-(4-(pyridin-4-ylmethoxy)benzyl)imidazolidin-1-yl}-butyrate (33)

Ethyl 2-(3-(4-hydroxybenzyl)-2-oxoimidazolidin-1-yl)-3-methylbutyrate (50 mg; 0.15 mmol) was dissolved in DMSO (1 ml). 4-Chloromethylpyridine hydrochloride (39 mg; 0.23 mmol), potassium carbonate (86 mg; 0.62 mmol) and potassium iodide (8 mg, 0.4 mmol) were successively added thereto. The mixture was heated at 50° C. for 3 h. Cooling to RT was followed by partitioning between water (10 ml) and EtOAc (10 ml). The phases were separated and the aqueous phase was extracted with EtOAc (3×; 5 ml). The combined organic phases were dried over $MgSO_4$, and the solvent was removed under reduced pressure. Purification of the residue by column chromatography ($SiO_2$) resulted in ethyl 3-methyl-2-{2-oxo-3-(4-(pyridin-4-ylmethoxy)benzyl)imidazolidin-1-yl}-butyrate (45 mg; 0.11 mmol). MS: 412.50 (M+H); $R_t$: 1.04 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 μL (YMC J'sphere ODS H80 20X2 1.4μ); 30° C.)

5.3 3-Methyl-2-{2-oxo-3-(4-(pyridin-4-ylmethoxy)benzyl)imidazolidin-1-yl}-butyric acid (34)

Ethyl 3-methyl-2-{2-oxo-3-(4-(pyridin-4-ylmethoxy)benzyl)imidazolidin-1-yl}-butyrate (45 mg; 0.11 mmol) was dissolved in methanol (1.5 ml) and cooled to 0° C. NaOH (1N, 5 ml) was added, and the mixture was allowed to warm to RT over the course of 3 h. The methanol was then removed under reduced pressure, and water (1.5 ml) and saturated $NaH_2PO_4$ solution (3 ml) were added to the residue. The solid was filtered off with suction and washed with water. Drying under reduced pressure at 60° C. resulted in 3-methyl-2-{2-oxo-3-(4-(pyridin-4-ylmethoxy)benzyl)imidazolidin-1-yl}-butyric acid (36 mg; 0.09 mmol). MS: 384.45 (M+H); $R_t$: 0.87 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 μL (YMC J'sphere ODS H80 20X2 1.4μ); 30° C.)

5.4 N-Hydroxy-3-methyl-2-[2-oxo-3-(4-(pyridin-4-ylmethoxy)benzyl)-imidazolidin-1-yl]butyramide; compound with TFA (35)

3-Methyl-2-{2-oxo-3-(4-(pyridin-4-ylmethoxy)benzyl)imidazolidin-1-yl}butyric acid (36 mg; 0.09 mmol) were dissolved in THF (5 ml) and cooled to 0° C. DIEA (66 μl; 0.37 mmol) and ethyl chloroformate (27 μl; 0.28 mmol) were successively added thereto. The mixture was allowed to reach RT over the course of 3 h. Then O-(trimethylsilyl)hydroxylamine 42 μl; 0.56 mmol) was added, and stirring was continued at RT for 15 h. The solvent was then removed under reduced pressure. The residue was taken up in dilute HCl (2 ml) and stirred for 10 min. The mixture was neutralized with dilute NaOH and extracted with $CHCl_3$/i-propanol (4:1; 3×; 10 ml). The combined organic phases were dried over $MgSO_4$, and the solvent was removed under reduced pressure. Purification of the residue by preparative HPLC purified resulted in N-hydroxy-3-methyl-2-{2-oxo-3-(4-(pyridin-4-ylmethoxy)benzyl)imidazolidin-1-yl}butyramide as trifluoroacetate (9 mg; 0.02 mmol). MS: 399.40 (M+H); $R_t$: 0.78 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 μL (YMC J'sphere ODS H80 20X2 1.4μ); 30° C.)

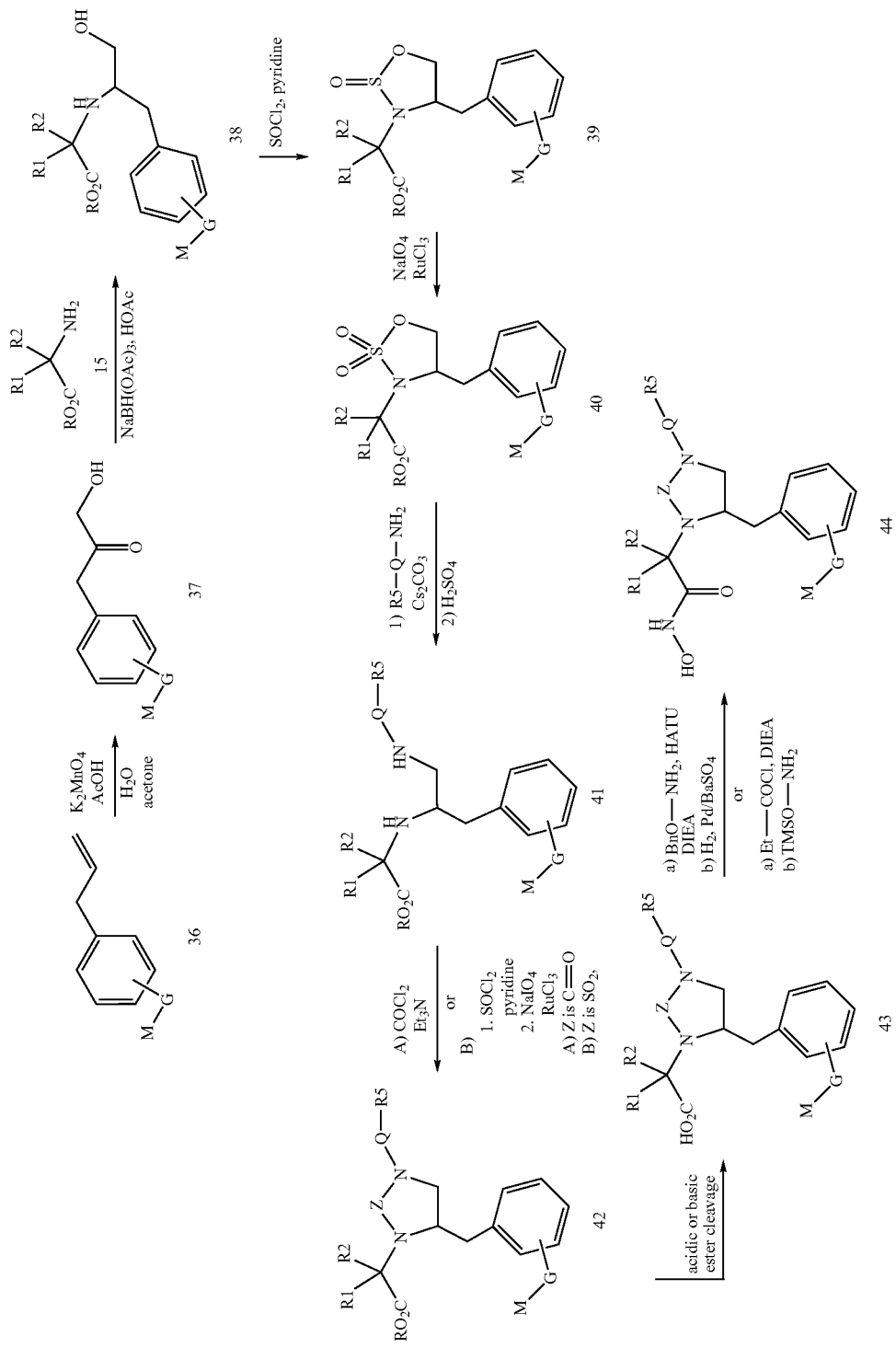

6.1 1-Hydroxy-3-(4-methoxyphenyl)propan-2-one (37)

4-Allylanisole (98%; 3.0 g; 19.86 mmol) was dissolved in glacial acetic acid (180 ml), water (180 ml) and acetone (180 ml). $KMnO_4$ (4.7 g; 29.79 mmol) was added over the course of 1 h. The mixture was then stirred at (RT) for 1 h. It was then decolorized with saturated $NaHCO_3$ solution. The reaction volume was reduced in a rotary evaporator. This was followed by extraction with $CH_2Cl_2$, washing of the organic phase with water and drying over $Na_2SO_4$. The solvent was then removed in a rotary evaporator. The oily residue was purified by column chromatography ($SiO_2$; EtOAc/n-heptane 1:2). 1-Hydroxy-3-(4-methoxyphenyl)propan-2-one was obtained as a white crystalline powder. MS: 81.20 (M+H); $R_t$: 0.83 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 µL (YMC J'sphere ODS H80 20X2 1.4µ); 30° C.)

6.2 t-Butyl 2-(1-hydroxymethyl-2-(4-methoxyphenyl)ethylamino)-3-methylbutyrate (38)

Valine t-butyl ester hydrochloride (302 mg; 1.45 mmol) was dissolved in a little 1N NaOH and extracted with $CH_2Cl_2$ (3×), and the combined organic phases were dried over $Na_2SO_4$. After concentration in a rotary evaporator, the free amine obtained in this way was dissolved in 1,2-dichloroethane (2.4 ml). Then, 1-hydroxy-3-(4-methoxyphenyl)propan-2-one (200 mg, 1.1 mmol) and glacial acetic acid (38 µl) were added. The mixture was stirred at RT for 1 h. NaBH(OAc)₃ (303 mg; 1.45 mmol) was added. This was followed by stirring at RT for 4 h. The reaction mixture was taken up in $CH_2Cl_2$ and washed with saturated $NaHCO_3$ solution, and the organic phase was dried over $Na_2SO_4$. Concentration in a rotary evaporator resulted in an oily residue which was purified by preparative HPLC. The acetonitrile was removed from the combined product fractions in a rotary evaporator, and saturated $NaHCO_3$ solution was added. This was followed by extraction with $CH_2Cl_2$ and drying over $Na_2SO_4$. Concentration in a rotary evaporator resulted in t-butyl 2-(1-hydroxymethyl-2-(4-methoxyphenyl)-ethylamino)-3-methylbutyrate (74 mg; 0.22 mmol). MS: 338.20 (M+H); $R_t$: 1.05 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 µL (YMC J'sphere ODS H80 20X2 1.4µ); 30° C.)

6.3 t-Butyl 2-(4-(4-methoxybenzyl)-2-oxo-(1,2,3) oxathiazolidin-3-yl)-3-methylbutyrate (39)

t-Butyl 2-(1-hydroxymethyl-2-(4-methoxyphenyl)ethylamino)-3-methylbutyrate (2.49 g; 7.4 mmol) was dissolved in $CH_2Cl_2$ (180 ml). The reaction solution was cooled to −78° C. Then pyridine (3 ml; 37 mmol) was added and subsequently thionyl chloride (0.64 ml; 8.88 mmol) was added dropwise. The reaction mixture was stirred for 1 h, during which the temperature was allowed to reach 0° C. It was taken up in $CH_2Cl_2$ and washed with aqueous HCl (1%; 2×) and $NaHCO_3$ solution. The organic phase was dried over $Na_2SO_4$ and concentrated in a rotary evaporator. The crude product was purified by filtration through silica gel (100 g). t-Butyl 2-(4-(4-methoxybenzyl)-2-oxo-(1,2,3)oxathiazolidin-3-yl)-3-methylbutyrate (2.35 g; 0.61 mmol) was obtained as a dark yellow oil. MS: 384.20 (M+H); $R_t$: 1.76 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 µL (YMC J'sphere ODS H80 20X2 1.4µ); 30° C.)

6.4 t-Butyl 2-(4-(4-methoxybenzyl)-2,2-dioxo-(1,2,3)oxathiazolidin-3-yl)-3-methylbutyrate (40)

t-Butyl 2-(4-(4-methoxybenzyl)-2-oxo-(1,2,3) oxathiazolidin-3-yl)-3-methylbutyrate (2.2 g; 5.7 mmol) was dissolved in acetonitrile (15 ml) and the reaction solution was cooled to 0° C. Then $NaIO_4$ (1.47 g; 6.8 mmol), $RuCl_3 \cdot H_2O$ (128.5 mg; 0.57 mmol) and water (15 ml) were added. The reaction solution was stirred at 0° C. for 5 minutes and then at RT for 30 minutes. This was followed by addition of $NaHCO_3$ solution, extraction with $CH_2Cl_2$ (3×) and drying of the organic phase over $NaSO_4$ and concentration in a rotary evaporator. The crude product was filtered through an $SiO_2$ cartridge (10 g). t-Butyl 2-(4-(4-methoxybenzyl)-2,2-dioxo-(1,2,3)oxathiazolidin-3-yl)-3-methylbutyrate (2.02 g; 5.0 mmol) was obtained as a yellow oil. MS: 417.45 (M+$NH_4^+$); $R_t$: 1.86 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 µL (YMC J'sphere ODS H80 20X2 1.4µ); 30° C.)

6.5 t-Butyl 2-(2-benzylamino-1-(4-methoxybenzyl) ethylamino)-3-methylbutyrate (41)

t-Butyl 2-(4-(4-methoxybenzyl)-2,2-dioxo-(1,2,3) oxathiazolidin-3-yl)-3-methylbutyrate (1.0 g; 2.5 mmol) was dissolved in acetonitrile (15 ml). $Cs_2CO_3$ (1.63 g; 5 mmol) and benzylamine (0.5 ml; 4.5 mmol) were added, The reaction mixture was stirred at 55° C. for 4 h. It was then allowed to reach RT, and the reaction mixture was filtered through a clarifying layer. The residue was washed with acetonitrile. The filtrate was concentrated and taken up in $CH_2Cl_2$ (10 ml). Aqueous $H_2SO_4$ (20%; 5 ml) was added, and the mixture was stirred at RT for 1.5 h. The phases were then separated, the aqueous phase was extracted with $CH_2Cl_2$ (2×), and the combined organic phases were dried over $Na_2SO_4$ and concentrated in a rotary evaporator. The crude product was stirred with $CH_2Cl_2/CH_3CN/Et_2O$ and concentrated. t-Butyl 2-(2-benzylamino-1-(4-methoxybenzyl)ethylamino)-3-methylbutyrate (1.15 g; 2.5 mmol) was obtained as a yellowish foam. MS: 427.20 (M+H); $R_t$: 1.42 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 µL (YMC J'sphere ODS H80 20X2 1.4µ); 30° C.)

6.6 t-Butyl 2-(3-benzyl-5-(4-methoxybenzyl)-2-oxoimidazolidin-1-yl)-3-methyl-butyrate (42)

t-Butyl 2-(2-benzylamino-1-(4-methoxybenzyl)ethylamino)-3-methylbutyrate (0.64 g; 1.5 mmol) was dissolved in toluene (40 ml). Triethylamine (457 µL; 3.3 mmol) and triphosgene (0.49 g; 1.65 mmol) were added. The reaction mixture was stirred at RT for 4.5 h. It was then washed with water (1×), saturated $NaHCO_3$ solution (1×) and again with water (1×). The organic phase was dried over $Na_2SO_4$ and concentrated in a rotary evaporator. The crude product was chromatographed on an $SiO_2$ cartridge (EtOAc/n-heptane 1:3). t-Butyl 2-(3-benzyl-5-(4-methoxybenzyl)-2-oxoimidazolidin-1-yl)-3-methylbutyrate (0.22 g, 0.48 mmol) was obtained as a yellow oil. MS: 453.20 (M+H); $R_t$: 1.94 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 µL (YMC J'sphere ODS H80 20X2 1.4µ); 30° C.)

6.7 2-(3-Benzyl-5-(4-methoxybenzyl)-2-oxoimidazolidin-1-yl)-3-methylbutyric acid (43)

t-Butyl 2-(3-benzyl-5-(4-methoxybenzyl)-2-oxoimidazolidin-1-yl)-3-methylbutyrate (0.22 g; 0.48 mmol) was dissolved in $CH_2Cl_2$ (2 ml), and the reaction solution was cooled to 0° C. Then TFA (2 ml) was added. The reaction mixture was stirred at 0° C. for 3 h. It was then concentrated in a rotary evaporator, and the residue was taken up with water and extracted with $CH_2Cl_2$ (3×). The organic phase was dried over $Na_2SO_4$ and concentrated in a rotary evaporator. 2-(3-Benzyl-5-(4-methoxybenzyl)-2-oxoimidazolidin-1-yl)-3-methylbutyric acid (0.18 g; 0.45 mmol) was obtained as a yellow oil. MS: 397.20 (M+H); $R_t$: 1.52 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 µL (YMC J'sphere ODS H80 20X2 1.4µ); 30° C.)

6.8 2-(3-Benzyl-5-(4-methoxybenzyl)-2-oxoimidazolidin-1-yl)-N-hydroxy-3-methylbutyramide (44)

2-(3-Benzyl-5-(4-methoxybenzyl)-2-oxoimidazolidin-1-yl)-3-methylbutyric acid (174 mg; 0.44 mmol) was dissolved in THF (4 ml). Ethyl chloroformate (42 µL; 0.53 mmol), N-ethylmorpholine (112 µL; 0.88 mmol) and O-trimethylsilyl-hydroxalanine (90%) were added. The reaction mixture was stirred at RT for 3 h and then concentrated in a rotary evaporator. The residue was taken up in $CH_2Cl_2$ and extracted with $H_2O$ (1×), and the organic phase was dried over $Na_2SO_4$ and concentrated in a rotary evaporator. The crude product was purified on an $SiO_2$ cartridge (50 g) ($CH_2Cl_2$/MeOH 50:1). Subsequent crystallization from diethyl ether/n-pentane resulted in 2-(3-benzyl-5-(4-methoxybenzyl)-2-oxoimidazolidin-1-yl)-N-hydroxy-3-methylbutyramide (92 mg; 0.23 mmol) as white crystals. MS: 412.20 (M+H); $R_t$: 1.35 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 µL (YMC J'sphere ODS H80 20X2 1.4µ); 30° C.)

Example 1

2-(3-(4-Benzyloxybenzyl)-2-oxoimidazolidin-1-yl)-N-hydroxy-3-methylbutyramide 2-(3-(4-Benzyloxybenzyl)-2-oxoimidazolidin-1-yl)-N-hydroxy-3-methylbutyramide (25 mg) was obtained from imidazolidin-2-one in analogy to the procedure in 3.1. MS: 398.15 (M+H); $R_t$: 1.30 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 µL (YMC J'sphere ODS H80 20X2 1.4µ); 30° C.)

Example 2

2-(3-(4-Benzyloxyphenyl)-2-oxoimidazolidin-1-yl)-N-hydroxy-3-methylbutyramide 2-(3-(4-Benzyloxyphenyl)-2-oxoimidazolidin-1-yl)-N-hydroxy-3-methylbutyramide (22 mg) was obtained from 2-oxazolidone in analogy to the procedure in 3.2. MS: 384.25 (M+H); $R_t$: 1.94 min (method: gradient acetonitrile+0.08% formic acid: $H_2O$+0.1% formic acid from 5:95 (0 min) to 95:5 (2.5 min) to 95:5 (3 min); flow rate 1.3 ml/min; column YMC Jsphere 33*2.1)

Example 3

2-(3-(3-Benzyloxybenzyl)-2-oxoimidazolidin-1-yl)-N-hydroxy-3-methylbutyramide 2-(3-(3-Benzyloxybenzyl)-2-oxoimidazolidin-1-yl)-N-hydroxy-3-methylbutyramide (8 mg) was obtained from valine t-butyl ester hydrochloride in analogy to the procedure in 3.3. MS: 398.15 (M+H); $R_t$: 1.46 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 µL (YMC J'sphere ODS H80 20X2 1.4µ); 30° C.)

Example 4

N-Hydroxy-3-methyl-2-(2-oxo-3-(4-phenoxybenzyl) imidazolidin-1-yl)-butyramide

N-Hydroxy-3-methyl-2-(2-oxo-3-(4-phenoxybenzyl)imidazolidin-1-yl)butyramide (14 mg) was obtained from valine t-butyl ester hydrochloride in analogy to the procedure in 3.3. MS: 384.15 (M+H); $R_t$: 1.45 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 µL (YMC J'sphere ODS H80 20X2 14µ); 30° C.)

Example 5

2-(3-(6-Benzyloxypyridin-3-ylmethyl)-2-oxoimidazolidin-1-yl)-N-hydroxy-3-methylbutyramide 2-(3-(6-Benzyloxypyridin-3-ylmethyl)-2-oxoimidazolidin-1-yl)-N-hydroxy-3-methylbutyramide (31 mg) was obtained from valine t-butyl ester hydrochloride in analogy to the procedure in 3.3. MS: 399.25 (M+H); $R_t$: 1.43 min (method: gradient acetonitrile+0.08% formic acid: $H_2O$+0.1% formic acid from 5:95 (0 min) to 95:5 (2.5 min) to 95:5 (3 min); flow rate 1.3 ml/min; column YMC Jsphere 33*2.1)

Example 6

2-(3-Biphenyl-4-ylmethyl-2-oxoimidazolidin-1-yl)-N-hydroxy-3-methylbutyramide 2-(3-Biphenyl-4-ylmethyl-2-oxoimidazolidin-1-yl)-N-hydroxy-3-methylbutyramide (101 mg) was obtained from valine t-butyl ester hydrochloride in analogy to the procedure in 3.3. MS: 398.29 (M+H); $R_t$: 1.92 min (method: gradient acetonitrile+0.08% formic acid: $H_2O$+0.1% formic acid from 5:95 (0 min) to 95:5 (2.5 min) to 95:5 (3 min); flow rate 1.3 ml/min; column YMC Jsphere 33*2.1)

Example 7

2-(3-Benzyl-5-(4-methoxyphenyl)-2-oxoimidazolidin-1-yl)-N-hydroxy-3-methylbutyramide 2-(3-Benzyl-5-(4-methoxyphenyl)-2-oxoimidazolidin-1-yl)-N-hydroxy-3-methylbutyramide (16 mg) was obtained from 1-(4-methoxyphenyl)ethanone in analogy to the proce-

Example 8

N-Hydroxy-2-(3-(4-hydroxybenzyl)-2-oxoimidazolidin-1-yl)-3-methylbutyramide

N-Hydroxy-2-(3-(4-hydroxybenzyl)-2-oxoimidazolidin-1-yl)-3-methylbutyramide (5 mg) was obtained from ethyl 2-(3-(4-benzyloxybenzyl)-2-oxoimidazolidin-1-yl)-3-methylbutyrate in analogy to the procedure in 3.5. MS: 308.21 (M+H); $R_t$: 1.29 min (method: gradient acetonitrile+0.08% formic acid: $H_2O$+0.1% formic acid from 5:95 (0 min) to 95:5 (2.5 min) to 95:5 (3 min); flow rate 1.3 ml/min; column YMC Jsphere 33*2.1)

Example 9

N-Hydroxy-2-(3-(3-hydroxybenzyl)-2-oxoimidazolidin-1-yl)-3-methylbutyramide

N-Hydroxy-2-(3-(3-hydroxybenzyl)-2-oxoimidazolidin-1-yl)-3-methylbutyramide (8 mg) was obtained from t-butyl 2-(3-(3-benzyloxybenzyl)-2-oxoimidazolidin-1-yl)-3-methylbutyrate in analogy to the procedure in 3.5. MS: 308.15 (M+H); $R_t$: 0.97 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 μL (YMC J'sphere ODS H80 20X2 1.4μ); 30° C.)

Example 10

N-Hydroxy-3-methyl-2-{2-oxo-3-(4-(pyridin-4-yl-methoxy)benzyl)imidazolidin-1-yl}-butyramide; compound with TFA N-Hydroxy-3-methyl-2-{2-oxo-3-(4-(pyridin-4-yl-methoxy)benzyl)imidazolidin-1-yl}-butyramide; compound with TFA (9 mg) was obtained from ethyl 2-(3-(4-benzyloxybenzyl)-2-oxoimidazolidin-1-yl)-3-methylbutyrate in analogy to the procedure in 3.5. MS: 399.40 (M+H); $R_t$: 0.78 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 μL (YMC J'sphere ODS H80 20X2 1.4μ); 30° C.)

Example 11

N-Hydroxy-3-methyl-2-[2-oxo-3-(4-(pyridin-3-yl-methoxy)benzyl)imidazolidin-1-yl]-butyramide with TFA N-Hydroxy-3-methyl-2-{2-oxo-3-(4-(pyridin-3-yl-methoxy)benzyl)imidazolidin-1-yl}-butyramide with TFA (6 mg) was obtained from ethyl 2-(3-(4-benzyloxybenzyl)-2-oxoimidazolidin-1-yl)-3-methylbutyrate in analogy to the procedure in 3.5. MS: 399.45 (M+H); $R_t$: 0.77 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 μL (YMC J'sphere ODS H80 20X2 1.4μ); 30° C.)

Example 12

N-Hydroxy-3-methyl-2-{2-oxo-3-(4-(pyridin-2-yl-methoxy)benzyl)imidazolidin-1-yl}butyramide with TFA N-Hydroxy-3-methyl-2-{2-oxo-3-(4-(pyridin-2-yl-methoxy)benzyl)imidazolidin-1-yl}-butyramide with TFA (6 mg) was obtained from ethyl 2-(3-(4-benzyloxybenzyl)-2-oxoimidazolidin-1-yl)-3-methylbutyrate in analogy to the procedure in 3.5. MS: 399.45 (M+H); $R_t$: 0.79 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 μL (YMC J'sphere ODS H80 20X2 1.4μ); 30° C.)

Example 13

2-(3-(4-But-2-ynyloxybenzyl)-2-oxoimidazolidin-1-yl)-N-hydroxy-3-methylbutyramide 2-(3-(4-But-2-ynyloxybenzyl)-2-oxoimidazolidin-1-yl)-N-hydroxy-3-methylbutyramide (4 mg) was obtained from ethyl 2-(3-(4-benzyloxybenzyl)-2-oxoimidazolidin-1-yl)-3-methylbutyrate in analogy to the procedure in 3.5. MS: 360.45 (M+H); $R_t$: 1.15 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 μL (YMC J'sphere ODS H80 20X2 1.4μ); 30° C.)

Example 14

N-Hydroxy-3-methyl-2-{3-(4-(2-methylquinolin-4-ylmethoxy)benzyl)-2-oxoimidazolidin-1-yl}butyramide with TFA N-Hydroxy-3-methyl-2-{3-(4-(2-methylquinolin-4-yl-methoxy)benzyl)-2-oxoimidazolidin-1-yl}-butyramide with TFA (4 mg) was obtained from ethyl 2-(3-(4-benzyloxybenzyl)-2-oxoimidazolidin-1-yl)-3-methylbutyrate in analogy to the procedure in 3.5. MS: 463.55 (M+H); $R_t$: 0.89 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 μL (YMC J'sphere ODS H80 20X2 1.4μ); 30° C.)

Example 15

2-(3-Benzyl-5-(4-methoxybenzyl)-2-oxoimidazolidin-1-yl)-N-hydroxy-3-methylbutyramide 2-(3-Benzyl-5-(4-methoxybenzyl)-2-oxoimidazolidin-1-yl)-N-hydroxy-3-methylbutyramide (92 mg) was obtained from 4-allylanisole in analogy to the procedure in 3.6. MS: 412.20 (M+H); $R_t$: 1.35 min (method: gradient 0 min 96% $H_2O$ (0.05% TFA) 2.0 min 95% acetonitrile, 95% acetonitrile to 2.4 min, 4% acetonitrile 2.45 min; flow rate 1 ml/min; column 0.4 μL (YMC J'sphere ODS H80 20X2 1.4μ); 30° C.)

Example 16

2-(3-(4-Benzyloxybenzyl)-5-(4-methoxybenzyl)-2-oxoimidazolidin-1-yl)-N-hydroxy-3-methylbutyramide 2-(3-(4-Benzyloxybenzyl)-5-(4-methoxybenzyl)-2-oxoimidazolidin-1-yl)-N-hydroxy-3-methylbutyramide (55 mg) was obtained from 4-allylanisole in analogy to the procedure in 3.6. MS: 518.29 (M+H); $R_t$: 2.54 min (method: gradient acetonitrile+0.05% TFA:H$_2$O+0.05% TFA from 5:95 (0 min) to 95:5 (3.4 min) to 95:5 (4.4 min); flow rate 1 ml/min; column YMC Jsphere 33*2)

Example 17

N-Hydroxy-2-(5-(4-methoxybenzyl)-3-methyl-2-oxoimidazolidin-1-yl)-3-methylbutyramide N-Hydroxy-2-(5-(4-methoxybenzyl)-3-methyl-2-oxoimidazolidin-1-yl)-3-methylbutyramide (80 mg) was obtained from 4-allylanisole in analogy to the procedure in 3.6. MS: 336.22 (M+H); $R_t$: 1.62 min (method: gradient acetonitrile+0.05% TFA:H$_2$O+0.05% TFA from 5:95 (0 min) to 95:5 (3.4 min) to 95:5 (4.4 min); flow rate 1 ml/min; column YMC Jsphere 33*2)

Example 18

2-(5-Benzo(1,3)dioxol-5-ylmethyl-3-(4-benzyloxybenzyl)-2-oxoimidazolidin-1-yl)-N-hydroxy-3-methylbutyramide 2-(5-Benzo(1,3)dioxol-5-ylmethyl-3-(4-benzyloxybenzyl)-2-oxoimidazolidin-1-yl)-N-hydroxy-3-methylbutyramide (110 mg) was obtained from 4-allylanisole in analogy to the procedure in 3.6. MS: 532.31 (M+H); $R_t$: 2.62 min (method: gradient acetonitrile+0.05% TFA:H$_2$O+0.05% TFA from 5:95 (0 min) to 95:5 (3.4 min) to 95:5 (4.4 min); flow rate 1 ml/min; column YMC Jsphere 33*2)

Example 19

2-(5-Benzo(1,3)dioxol-5-ylmethyl-3-benzyl-2-oxoimidazolidin-1-yl)-N-hydroxy-3-methylbutyramide 2-(5-Benzo(1,3)dioxol-5-ylmethyl-3-benzyl-2-oxoimidazolidin-1-yl)-N-hydroxy-3-methylbutyramide (100 mg) was obtained from 4-allylanisole in analogy to the procedure in 3.6. MS: 426.26 (M+H); $R_t$: 2.07 min (method: gradient acetonitrile+0.05% TFA:H$_2$O+0.05% TFA from 5:95 (0 min) to 95:5 (3.4 min) to 95:5 (4.4 min); flow rate 1 ml/min; column YMC Jsphere 33*2)

Example 20

2-(5-(4-Benzyloxybenzyl)-3-(4-methoxybenzyl)-1,1-dioxo-(1,2,5)thiadiazolidin-2-yl)-N-hydroxy-3-methylbutyramide 2-(5-(4-Benzyloxybenzyl)-3-(4-methoxybenzyl)-1,1-dioxo-(1,2,5)thiadiazolidin-2-yl)-N-hydroxy-3-methylbutyramide (17 mg) was obtained from 4-allylanisole in analogy to the procedure in 3.6. MS: 554.37 (M+H); $R_t$: 2.57 min (method: gradient acetonitrile+0.05% TFA:H$_2$O+0.05% TFA from 5:95 (0 min) to 95:5 (3.4 min) to 95:5 (4.4 min); flow rate 1 ml/min; column YMC Jsphere 33*2)

PHARMACOLOGICAL EXAMPLES

The activity of the cyclic urea derivatives of the invention was tested in various in vitro assay systems for inhibitory activity on the proteases ADAMTS-4 and TNFα-converting enzyme (TACE) and on matrix-degrading metalloproteases (MMP13).

The ADAMTS-4 activity was measured using a recombinantly prepared human ADAMTS-4 protease and the rAgg1mut substrate. The rAgg1mut substrate comprises the interglobular domain of the human aggrecan molecule fused N-terminally to a FLAG sequence and fused C-terminally to a human IgG Fc portion. In the interglobular domain there is a specific cleavage site for ADAMTS-4, cleavage of which generates a new N-terminal epitope which can be measured by means of a neo-epitope-specific monoclonal antibody in an ELISA test system (Hörber, C., Büttner, F H., Kern, C., Schmiedeknecht, G. & Bartnik, E. (2000), Matrix Biology 19, 533-543).

The activity in relation to TACE was measured using a commercially available, recombinantly prepared TACE protease (R&D Systems) and the substrate MCA-ProLeuAla-GlnAlaVal-Dpa-ArgSerSerSerArg-NH2 (Bachem). Cleavage of the TACE-specific substrate is measured in a fluorimeter with the wavelengths Ex 320 nm/Em 405 nm, and the amount of cleaved substrate is determined from a calibration plot.

The activities in relation to MMP13 were measured using recombinantly prepared enzymes from various manufacturers (Biotrend, Roche, Boehringer Mannheim) and with various MMP-specific peptide substrates (Bachem). Cleavage of the MMP-specific substrates was measured after APMA activation of the proteases at pH 7.5 or pH 6.5 in a fluorimeter at the wavelengths of Ex 340 nm/Em 405 nm.

The proteoglycan degradation was determined using primary bovine chondrocytes which were isolated from the cartilage of the metacarpophalangeal joint of cattle about 6 months old and cultured in an alginate matrix at 37° C. and 5% CO$_2$ for 3 weeks. Stimulation of ~160 000 cells with 5 ng/ml human IL1α was followed after 16 hours by determination of the liberated amount of proteoglycan by means of a commercially available dimethylmethylene blue dye test system (Biocolor Ltd.).

Inhibition of ADAMTS-4 Activity (IC50 in µM):

| | Example | | | | | | | | | | | | |
|---|---|---|---|---|---|---|---|---|---|---|---|---|---|
| | 1 | 2 | 4 | 5 | 6 | 9 | 10 | 11 | 12 | 14 | 15 | 16 | 18 |
| ADAMTS-4 | 2.1 | 55 | 1.33 | 10 | 9.06 | 72.39 | 0.9 | 7.8 | 7.0 | 1.14 | 17 | 1.39 | 3.16 |

Inhibition of MMP 13 Activity (IC50 in μM):

| | Example | | | | | | | | | | |
|---|---|---|---|---|---|---|---|---|---|---|---|
| | 1 | 4 | 7 | 10 | 11 | 15 | 16 | 17 | 18 | 19 | 20 |
| MMP13 | 5.0 | 0.08 | 0.01 | 4.0 | 5.4 | 0.4 | 0.42 | 3.17 | 0.6 | 0.34 | 3.58 |

Inhibition of TACE activity (IC50 in μM):

| | Example | | | | | | | | | | | | |
|---|---|---|---|---|---|---|---|---|---|---|---|---|---|
| | 1 | 3 | 4 | 7 | 9 | 10 | 11 | 12 | 13 | 14 | 15 | 16 | 18 | 19 |
| TACE | 2.47 | 2.0 | 5.0 | 9.0 | 3.04 | 1.14 | 3 | 8 | 5 | 0.01 | 8 | 3.08 | 1.9 | 9.29 |

Inhibition of Proteoglycan Liberation from IL1α-Stimulated Primary Bovine Chondrocyte Cultures:

| | Example | | | |
|---|---|---|---|---|
| | 1 | 10 | 14 | 16 |
| Inhibition of proteoglycan liberation (IC50 in μM) | >50 | >50 | 12.9 | 25.5 |

(> = more than)

What is claimed is:
1. A compound of the formula I:

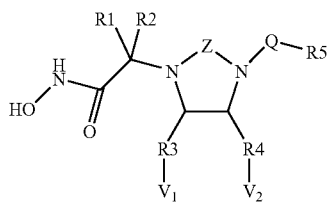

(I)

and/or all stereoisomeric forms of the compound of the formula I and/or mixtures of these forms in any ratio, and/or a physiologically tolerated salt of the compound of the formula I, wherein, Z is —C(O)—,
R1 and R2 are identical or different and are independently of one another
hydrogen atom or —($C_1$-$C_4$)-alkyl, or R1 and R2 form together with the carbon atom to which they are respectively bonded —($C_3$-$C_6$)-cycloalkyl,
R3 and R4 are identical or different and are independently of one another: a covalent bond, —(CH$_2$)$_m$— or —($C_1$-$C_3$)-alkylene-O—($C_0$-$C_3$)-alkylene-, in which
m is the integer 1, and in which the alkylene radical which is formed by
—(CH$_2$)$_m$— is unsubstituted or substituted once by —OH,
V$_2$ is hydrogen atom,
V$_1$ and R5 are identical or different and are independently of one another
hydrogen atom, —(C6-C14)-aryl in which aryl is phenyl and is unsubstituted or substituted once or twice by R8 or the radical -G-M, or a mono- or bicyclic 4- to 15-membered heterocycle in which heterocycle is a radical from the series benzodioxol, quinolinyl or pyridyl,
in which the heterocycle is unsubstituted or substituted once, twice or three times by R8 or the radical -G-M,
M is:
hydrogen atom, —(C6-C14)-aryl in which aryl is phenyl and is unsubstituted or substituted once or twice by R8, or a mono- or bicyclic 4- to 15-membered heterocycle in which heterocycle is as defined above and in which the heterocycle is unsubstituted or substituted once, twice or three times by R8,
R8 is halogen, —OH or —(C1-C4)-alkyl or —O—(C1-C4)-alkyl,
G is:
covalent bond, —(C0-C3)-alkylene-O—(C0-C3)-alkylene- or —(C0-C3)-alkylene-O—(C2-C4)-alkenylene-, and
Q is:
covalent bond or —(C1-C3)-alkylene, on condition that at least one of the radicals V1 or R5 is —(C6-C14)-aryl or a mono- or bicyclic 4- to 15-membered heterocycle, in which aryl or heterocycle are unsubstituted or substituted once or twice by R8 or the radical -G-M; wherein the compound is
selected from the following compounds:
2-[3-(4-benzyloxybenzyl)-2-oxoimidazolidin-1-yl]-N-hydroxy-3-methylbutyramide,
2-[3-(4-benzyloxyphenyl)-2-oxoimidazolidin-1-yl]-N-hydroxy-3-methylbutyramide,
2-[3-(3-benzyloxybenzyl)-2-oxoimidazolidin-1-yl]-N-hydroxy-3-methylbutyramide,
N-hydroxy-3-methyl-2-[2-oxo-3-(4-phenoxybenzyl)imidazolidin-1-yl]-butyramide,
2-[3-(6-benzyloxypyridin-3-ylmethyl)-2-oxoimidazolidin-1-yl]-N-hydroxy-3-methylbutyramide,
2-(3-biphenyl-4-ylmethyl-2-oxoimidazolidin-1-yl)-N-hydroxy-3-methylbutyramide,
2-[3-benzyl-5-(4-methoxyphenyl)-2-oxoimidazolidin-1-yl]-N-hydroxy-3-methylbutyramide,
N-hydroxy-2-[3-(4-hydroxybenzyl)-2-oxoimidazolidin-1-yl]-3-methylbutyramide, N-hydroxy-2-[3-(3-hydroxybenzyl)-2-oxoimidazolidin-1-yl]-3-methylbutyramide, N-hydroxy-3-methyl-2-{2-oxo-3-[4-(pyridin-4-ylmethoxy)benzyl]imidazolidin-1-yl}butyramide with trifluoroacetic acid (TFA), N-hydroxy-3-methyl-2-{2-oxo-3-[4-(pyridin-3-ylmethoxy)benzyl]imidazolidin-1-yl}butyramide with TFA, N-hydroxy-3-methyl-2-{2-oxo-3-[4-(pyridin-2-ylmethoxy)benzyl]imidazolidin-1-yl}butyramide with TFA, 2-[3-(4-but-2-ynyloxybenzyl)-2-oxoimidazolidin-1-yl]-N-hydroxy-3-methylbutyramide, N-hydroxy-3-methyl-2-{3-[4-(2-methylquinolin-4-ylmethoxy)benzyl]-2-oxoimidazolidin-1-yl}butyramide with TFA, 2-[3-benzyl-5-(4-methoxybenzyl)-2-oxoimidazolidin-1-yl]-N-hydroxy-3-methylbutyramide, 2-[3-(4-benzyloxybenzyl)-5-(4-methoxybenzyl)-2-oxoimidazolidin-1-yl]-N-hydroxy-3-methylbutyramide, N-hydroxy-2-[5-(4-methoxybenzyl)-3-methyl-2-oxoimidazolidin-1-yl]-3-methylbutyramide, 2-[5-benzo[1,3]dioxol-5-ylmethyl-3-(4-benzyloxybenzyl)-2-oxoimidazolidin-1-yl]-N-hydroxy-3-methylbutyramide, 2-(5-benzo[1,3]dioxol-5-ylmethyl-3-benzyl-2-oxoimidazolidin-1-yl)-N-hydroxy-3-methylbutyramide or 2-[3-(4-benzyloxyphenyl)-2-oxo-[1,3]diazepan-1-yl]-N-hydroxy-3-methyl-butyramide.

2. A medicament having an effective amount of at least one compound of the formula I as claimed in claim 1 together with a pharmaceutically suitable and physiologically tolerated carrier, additive and/or other active substances and excipients.

* * * * *